(12) United States Patent
Fujisawa et al.

(10) Patent No.: US 9,632,212 B2
(45) Date of Patent: Apr. 25, 2017

(54) MEDICAL DEVICE AND METHOD FOR PRODUCING THE SAME

(75) Inventors: Kazuhiko Fujisawa, Otsu (JP); Rumiko Kitagawa, Otsu (JP); Masataka Nakamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 116 days.

(21) Appl. No.: 14/238,993

(22) PCT Filed: Aug. 10, 2012

(86) PCT No.: PCT/JP2012/070437
§ 371 (c)(1),
(2), (4) Date: Feb. 14, 2014

(87) PCT Pub. No.: WO2013/024801
PCT Pub. Date: Feb. 21, 2013

(65) Prior Publication Data
US 2014/0198295 A1    Jul. 17, 2014

(30) Foreign Application Priority Data

Aug. 17, 2011  (JP) ................ 2011-178658

(51) Int. Cl.
| G02B 1/04 | (2006.01) |
| A61L 27/34 | (2006.01) |
| B29D 11/00 | (2006.01) |
| G02C 7/04 | (2006.01) |
| G02B 1/18 | (2015.01) |

(52) U.S. Cl.
CPC .............. *G02B 1/043* (2013.01); *A61L 27/34* (2013.01); *B29D 11/00038* (2013.01); *G02B 1/18* (2015.01); *G02C 7/04* (2013.01); *A61L 2400/10* (2013.01); *A61L 2420/02* (2013.01); *A61L 2420/08* (2013.01); *A61L 2430/16* (2013.01)

(58) Field of Classification Search
CPC ..... B29D 11/00038; G02B 1/043; G02B 7/04
See application file for complete search history.

(56) References Cited

U.S. PATENT DOCUMENTS

| 4,153,641 A | 5/1979 | Deichert et al. |
| 4,277,595 A | 7/1981 | Deichert et al. |
| 4,543,398 A | 9/1985 | Bany et al. |
| 4,954,586 A | 9/1990 | Toyoshima et al. |
| 5,714,557 A * | 2/1998 | Kunzler .................. C07F 7/085 523/106 |
| 5,760,100 A * | 6/1998 | Nicolson ................ G02C 7/049 351/159.33 |
| 5,998,498 A | 12/1999 | Vanderlaan et al. |
| 6,451,871 B1 * | 9/2002 | Winterton ................ C08J 7/047 264/1.32 |
| 6,921,802 B2 * | 7/2005 | Kunzler ................ C08F 283/12 526/279 |
| 9,046,644 B2 * | 6/2015 | Nakamura .......... C08F 290/068 |
| 2001/0049400 A1 | 12/2001 | Alli et al. |
| 2002/0006521 A1 | 1/2002 | Shimoyama et al. |
| 2004/0047979 A1 | 3/2004 | Qiu et al. |
| 2007/0149699 A1 * | 6/2007 | Matsumoto ............. C08F 30/08 524/556 |
| 2008/0174035 A1 | 7/2008 | Winterton |
| 2012/0314183 A1 | 12/2012 | Nakamura et al. |
| 2014/0198294 A1 | 7/2014 | Nakamura et al. |

FOREIGN PATENT DOCUMENTS

| CA | 1102484 | 6/1981 |
| JP | 54-24047 | 2/1979 |
| JP | 54-081363 | 6/1979 |
| JP | 56-51715 | 5/1981 |
| JP | 59-229524 A | 12/1984 |
| JP | 02-188717 | 7/1990 |
| JP | 04-318010 A | 11/1992 |
| JP | 05-5861 A | 1/1993 |
| JP | 05-215996 | 8/1993 |
| JP | 11-316358 | 11/1999 |
| JP | 2002-501211 | 1/2002 |
| JP | 2002-047365 A | 2/2002 |
| JP | 2002-311395 A | 10/2002 |
| JP | 2003-513118 A | 4/2003 |
| JP | 2005-538418 A | 12/2005 |
| JP | 2006-003827 A | 1/2006 |
| JP | 2006-201263 | 8/2006 |
| JP | 2008-083649 A | 4/2008 |
| JP | 2009-540369 A | 11/2009 |
| JP | 2010-032992 A | 2/2010 |
| WO | WO 99/35520 | 7/1999 |
| WO | 0127174 | 4/2001 |
| WO | WO 2007/146137 | 12/2007 |
| WO | WO 2011/102356 A1 | 8/2011 |

OTHER PUBLICATIONS

International Search Report dated Oct. 30, 2012, Application No. PCT/JP2012/070437.
Extended European Search Report dated Mar. 16, 2015 for European Application No. 12824213.8.

\* cited by examiner

*Primary Examiner* — Margaret Moore
(74) *Attorney, Agent, or Firm* — RatnerPrestia

(57) ABSTRACT

To provide a medical device which is excellent in wettability and lubricity and is also scarcely broken since it is soft, by a medical device in which a layer made of an acidic polymer and a basic polymer is formed on at least a part of a surface of a low water content soft base material, the low water content soft base material containing, as a main component, a copolymer containing a monofunctional monomer component M having one polymerizable functional group and one silicone moiety per molecule.

15 Claims, 2 Drawing Sheets

MEDICAL DEVICE AND METHOD FOR PRODUCING THE SAME

CROSS REFERENCE TO RELATED APPLICATIONS

This is the U.S. National Phase application of PCT International Application No. PCT/JP2012/070437, filed Aug. 10, 2012, and claims priority to Japanese Patent Application No. 2011-178658, filed Aug. 17, 2011, the disclosures of each of these applications being incorporated herein by reference in their entireties for all purposes.

FIELD OF THE INVENTION

The present invention relates to a medical device, and a method for producing the same.

BACKGROUND OF THE INVENTION

One of medical devices includes a soft contact lens (soft lens for eye). A hydrogel material having a water content of about 25 to 80% is commonly used in the commercially available soft contact lens. However, since the low water content soft contact lens made of the hydrogel material contains water, there arises a phenomenon in which water is vaporized from the contact lens. Thereby, certain fixed proportions of contact lens wearers felt dry more strongly as compared with the case of the naked eye, and thus felt uncomfortable. Among these contact lens wearers, some persons complained a condition of so-called contact lens-related dry eye. Since a water-containing soft contact lens made of a hydrogel material is likely to be contaminated with components in a lacrimal fluid and also contains a large amount of water, there was also a risk of the growth of bacteria.

There has been known, as a highly oxygen permeable low water content soft contact lens, for example, a silicone rubber lens obtained by a method of adding a platinum-based catalyst to a mixture of polydimethylsiloxane in which both ends of the molecular chain are blocked with a vinylmethylsilyl group, and methyl hydrogen polysiloxane, followed by heat-curing using a molding method (see Patent Literature 1).

Patent Literatures 2 to 7 also disclose a highly oxygen permeable contact lens material composed mainly of polysiloxane having a plurality of polymerizable functional groups, or TRIS type polysiloxane having a polymerizable functional group at one end. Of these, Patent Literature 6 discloses a contact lens material made of a polymer obtained by polymerizing a difunctional organosiloxane macromer alone, or a polymer obtained by copolymerizing a difunctional organosiloxane macromer with the other monomers, and also discloses, as a monomer to be used in copolymerization, an acrylic acid fluoroalkyl ester or a methacrylic acid fluoroalkyl ester, and an acrylic acid alkyl ester or a methacrylic acid alkyl ester.

However, the following problems also lie in a conventional highly oxygen permeable low water content soft contact lens. First, a silicone rubber lens has such a drawback that a hydrophilized layer formed so as to improve hydrophobicity of the surface of the lens is peeled, or adhesion of the lens to the cornea occurs due to too large resilience, and thus the silicone rubber lens had not widely been put into practice.

A material composed mainly of polysiloxane having a plurality of polymerizable functional groups has high oxygen permeability and also has flexibility, and the material is considered to be one of materials which are suitable for a contact lens. However, since tackiness is left on the surface of the lens after polymerization, the lens may adhere to the cornea and is also insufficient in balance between flexibility of the lens and mechanical properties such as folding resistance.

Patent Literature 7 discloses, as a material of a non-hydrous soft contact lens, a polymer containing an alkoxysilane and a silicone monomer as constituents. Among these, the alkoxysilane is likely to cause hydrolysis or condensation, and functions as a crosslinking agent when condensation occurs, leading to an increase in elastic modulus, thus causing a problem in which comfort becomes worse since a contact lens becomes hard. The silicone monomer had a problem that, if a silicone moiety has a branched structure, shape recovery properties of a contact lens deteriorate when the content of the silicone monomer increases.

There have been known various methods for modification of a surface of a medical device. Among these methods, there is known a method in which two polymer materials, each having an opposite charge, are coated and accumulated in a layer by layer fashion (see, for example, Patent Literatures 8 to 10). Among these methods, a method of alternately forming layers made of two polymer materials, each having an opposite electric charge, in a layer by layer fashion by coating is called an LbL method, and it is considered that each layer of the material is noncovalently bonded to the other layer made of a different material. However, the highly oxygen permeable soft lens for eye in which utility of the method is clearly shown is made only of a silicone hydrogel material, and utility to the low water content soft lens for eye has not been known. Conventional LbL coating was carried out to obtain a multi-layered structure constituted from about 4 to 20 layers, and thus the production process may increase, to cause an increase in production costs.

PATENT LITERATURE

[Patent Literature 1]
Japanese Unexamined Patent Publication (Kokai) No. 54-81363
Patent Literature 2]
Japanese Unexamined Patent Publication (Kokai) No. 54-24047
[Patent Literature 3]
Japanese Unexamined Patent Publication (Kokai) No. 56-51715
[Patent Literature 4]
Japanese Unexamined Patent Publication (Kokai) No. 59-229524
[Patent Literature 5]
Japanese Unexamined Patent Publication (Kokai) No. 2-188717
[Patent Literature 6]
Japanese Unexamined Patent Publication (Kokai) No. 5-5861
[Patent Literature 7]
Kohyo (National Publication of Translated Version) No. 2002-311395
[Patent Literature 8]
Kohyo (National Publication of Translated Version) No. 2002-501211

[Patent Literature 9]
Kohyo (National Publication of Translated Version) No. 2005-538418
[Patent Literature 10]
Kohyo (National Publication of Translated Version) No. 2009-540369

SUMMARY OF THE INVENTION

The present invention has been made in view of the above problems and provides a medical device which is excellent in wettability and lubricity, and significantly reduce or avoid a phenomenon of adhesion to the cornea during wear, and is also scarcely broken since it is soft. The present invention also provides a method to produce a medical device in a simple process at low costs.

The present invention includes the following constitutions.

The present invention is directed to a medical device in which a layer made of an acidic polymer and a basic polymer is formed on at least a part of a low water content soft base material, the low water content soft base material containing, as a main component, a copolymer containing a monofunctional monomer component M having one polymerizable functional group and one silicone moiety per molecule.

The monofunctional monomer component M preferably has a number average molecular weight of 300 to 120,000. The monofunctional monomer component M is preferably selected from a component represented by the following formula (M1):

[Chemical Formula 1]

$$X^3-L^3-\underset{R^{16}}{\overset{R^{15}}{\underset{|}{\overset{|}{Si}}}}-O-\left[\underset{R^{12}}{\overset{R^{11}}{\underset{|}{\overset{|}{Si}}}}-O\right]_c-\left[\underset{R^{14}}{\overset{R^{13}}{\underset{|}{\overset{|}{Si}}}}-O\right]_d-\underset{R^{18}}{\overset{R^{17}}{\underset{|}{\overset{|}{Si}}}}-R^{19} \quad (M1)$$

wherein $X^3$ represents a polymerizable functional group; $R^{11}$ to $R^{19}$ each independently represents a substituent selected from hydrogen, an alkyl group having 1 to 20 carbon atoms, a phenyl group, and a fluoroalkyl group having 1 to 20 carbon atoms; $L^3$ represents a divalent group; and c and d each independently represents an integer of 0 to 700, provided that c and d are not simultaneously 0.

The base material preferably contains, as a main component:
(1) a copolymer containing the component M and the following component A, or
(2) a copolymer containing the component M, the following components A and B:
    component A: a polysiloxane compound having a plurality of polymerizable functional groups per molecule and a number average molecular weight of 6,000 or more, and
    component B: a polymerizable monomer having a fluoroalkyl group.

The present invention is also directed to a method for producing a medical device, which includes the following steps 1a to 3a in this order:
<Step 1a>
Step of polymerizing a mixture containing a component M which is a monofunctional monomer having one polymerizable functional group and one silicone moiety per molecule to obtain a molding;
<Step 2a>
Step of bringing the molding into contact with a basic polymer solution, and then washing the molding to remove the surplus basic polymer solution; and
<Step 3a>
Step of bringing the molding into contact with an acidic polymer solution, and then washing the molding to remove the surplus acidic polymer solution.

The present invention is also directed to a method for producing a medical device, which includes the following steps 1b to 4b in this order:
<Step 1b>
Step of polymerizing a mixture containing a component M which is a monofunctional monomer having one polymerizable functional group and one silicone moiety per molecule to obtain a molding;
<Step 2b>
Step of bringing the molding into contact with an acidic polymer solution, and then washing the molding to remove the surplus acidic polymer solution;
<Step 3b>
Step of bringing the molding into contact with a basic polymer solution, and then washing the molding to remove the surplus basic polymer solution; and
<Step 4b>
Step of bringing the molding into contact with an acidic polymer solution, and then washing the molding to remove the surplus acidic polymer solution.

Since medical device of the present invention is excellent in lubricity and wettability, it is possible to significantly reduce or avoid a phenomenon of adhesion to the cornea during wear, which has hitherto been regarded as a problem in a conventional low water content soft lens for eye. Since the medical device of the present invention has low water content, it is also possible to reduce a risk of the growth of bacteria. Furthermore, the medical device of the present invention has the effect of exhibiting excellent mechanical properties including both softness and breakage resistance, which could not been achieved by a conventional medical device, by controlling elastic modulus and elongation of a base material within a desired range. The medical device of the present invention also exerts the effect of achieving excellent shape recovery properties by decreasing a zero-stress time.

DETAILED DESCRIPTION OF EMBODIMENTS OF THE INVENTION

Figure 1:
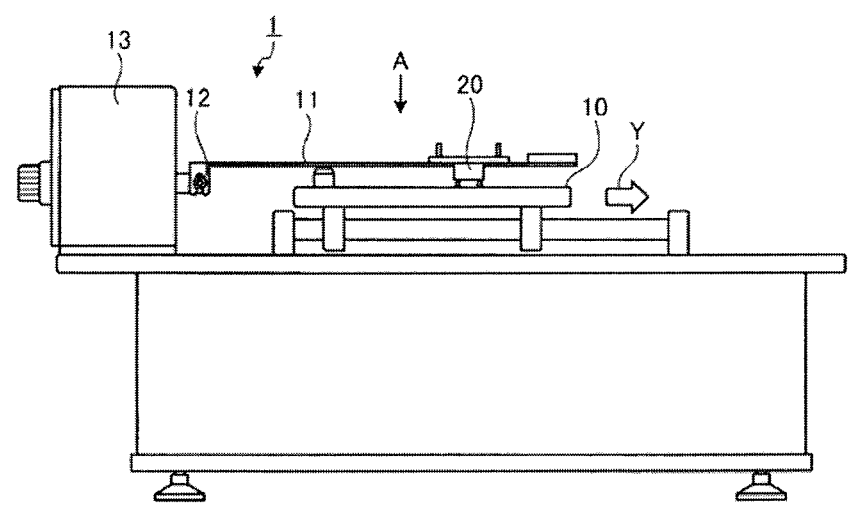
FIG. 1 is a schematic view showing an apparatus for measuring a surface friction coefficient of a sample of a medical device according to Example of the present invention, provided that FIG. 1 shows a state where a measurement jig and a friction block are fitted as standard equipment.

The medical device used in the present invention refers to a device which is used for medical purposes, and is used in contact with the patient, or which is used in contact with tissues collected from the patient, for example, blood or other body fluids, for example, a lens for eye or a skin material. Suitably, the medical device includes a lens for eye, an endoscope, a catheter, an infusion tube, a gas transfer tube, a stent, a sheath, a cuff, a tube connector, an access port, a drainage bag, a blood circuit, a skin material, or a drug carrier.

In the medical device of the present invention, low water content means that the water content is 10% by mass or less. Soft means that elastic modulus (tensile elastic modulus) is 10 MPa or less.

As used herein, the water content is given from the mass of a film-shaped specimen in a dry state (mass in a dry state) and the mass of the specimen in a wet state (mass in a wet state) by [((mass in a wet state)−(mass in a dry state))/(mass in a wet state)]×100.

The medical device of the present invention has features such as less feeling of dryness of wearers and excellent comfort when used as a lens for eye because of its low water content. The medical device of the present invention has a merit such as low risk of the growth of bacteria because of its low water content. The water content is more preferably 5% or less, still more preferably 2% or less, and most preferably 1% or less. Too high water content is not preferred since feeling of dryness of eyes of persons wearing a lens for eye may increase or risk of the growth of bacteria may become higher.

Elastic modulus (tensile elastic modulus) of the medical device of the present invention is preferably from 0.01 to 1.00 MPa, more preferably from 0.1 to 0.8 MPa, still more preferably from 0.1 to 0.7 MPa, even more preferably from 0.2 to 0.6 MPa, and most preferably from 0.2 to 0.55 MPa. When the tensile elastic modulus is too small, it may become difficult to handle since the lens is too soft. When the tensile elastic modulus is too large, comfort may become worse in the case of contacting with the skin of the patient or wearing a lens since the device is too hard. It is preferred that the elastic modulus becomes 1 MPa or less since satisfactory comfort can be obtained. The elastic modulus is measured by a specimen in a wet state.

Tensile elongation (elongation at break) of the medical device of the present invention is preferably from 100% to 1,000%, and more preferably from 200% to 700%. It is not preferred that the elongation is too small since the medical device is likely to be broken. It is not preferred that the elongation is too large since the medical device tends to be deformed. The elongation is measured by a specimen in a wet state.

It is important that medical device of the present invention is excellent in wettability of a surface, from the viewpoint of compatibility with the living body (biocompatibility). Particularly in the case of a lens for eye, from the viewpoint of preventing adhesion to the cornea of wearers, dynamic contact angle (advancing angle, immersion rate of 0.1 mm/sec) is preferably 100° or less, more preferably 90° or less, and still more preferably 80° or less. From the viewpoint of preventing adhesion to the cornea of wearers, the dynamic contact angle is preferably lower, and is preferably 65° or less, more preferably 60° or less, still more preferably 55° or less, even more preferably 50° or less, and most preferably 45° or less. The dynamic contact angle is measured relative to a borate buffer using a specimen in a state of being wetted with the borate buffer.

It is important that the medical device of the present invention is excellent in wettability of a surface, from the viewpoint of compatibility with the living body. From such viewpoint, liquid film retention time of a surface of a medical device is preferably long. As used herein, the liquid film retention time is the time during which a liquid film on a surface of a medical device (a diameter direction in the case of a lens for eye) is held without being broken, when the medical device immersed in a borate buffer is pulled up from the borate buffer and then held in air so that a diameter direction becomes vertical. The liquid film retention time is preferably 5 seconds or more, more preferably 10 seconds or more, and most preferably 20 seconds or more. As used herein, the diameter is the diameter of a circle composed of an edge portion of a lens. The liquid film retention time is measured using a sample in a state of being wetted with a borate buffer.

From the viewpoint of facilitating movement when contacted with a surface of the body tissue and preventing adhesion to the cornea of wearers particularly in the case of a lens for eye, the surface of the medical device preferably has excellent lubricity.

As an indicator representing the lubricity, the below-mentioned surface friction coefficient ratio (Qa and Qb) measured by the method mentioned in Examples of the present description are preferably smaller. The surface friction coefficient ratio (Qa) in a state of being wetted with a borate buffer of the medical device of the present invention is preferably 2 or less, more preferably 1.6 or less, and still more preferably 1 or less, provided that Qa=MIUa/MIUo: where MIUa represents a coefficient of surface friction between the medical device and a smooth quartz glass plate in a state of being wetted with the borate buffer; and MIUo represents a coefficient of surface friction between "ACUVUE® OASYS" and a smooth quartz glass plate in a state of being wetted with the borate buffer.

The smaller the surface friction coefficient ratio Qa becomes, the better since surface friction decreases, leading to a smaller influence exerted on the living body in the case of generating rubbing with the living body (for example, cornea or palpebral conjunctiva in the case of a contact lens). In that sense, the surface friction coefficient ratio Qa is preferably 1 or less, more preferably 0.8 or less, and most preferably 0.6 or less.

The surface friction coefficient ratio (Qb) in a state of being wetted with a saline is preferably 3 or less, more preferably 2 or less, and still more preferably 1.5 or less, provided that Qb=MIUb/MIUo: where MIUb represents a coefficient of surface friction between the medical device and a smooth quartz glass plate in a state of being wetted with the saline.

It has been found that, in a medical device of the present invention, Qb tends to become larger than Qa, and Qb sometimes becomes significantly larger. However, the saline is a liquid which resembles a body fluid (for example, lacrimal fluid in the case of a contact lens). From the viewpoint of preventing adhesion of the medical device to a surface of the living body (cornea in the case of a lens for eye), a surface friction coefficient ratio (Qb) in a state of being wetted with a saline is also preferably small.

The smaller the surface friction coefficient ratio Qb becomes, the better since surface friction decreases, leading to a smaller influence exerted on the living body in the case of generating rubbing with the living body (for example, cornea or palpebral conjunctiva in the case of a contact lens). In that sense, the surface friction coefficient ratio Qb is preferably 1.5 or less, more preferably 1.0 or less, and most preferably 0.8 or less.

In the medical device of the present invention, a difference (Qb−Qa) between a surface friction coefficient ratio Qb in a state of being wetted with a saline and a surface friction coefficient ratio Qa in a state of being wetted with a borate buffer is preferably 1.6 or less, more preferably 1.3 or less, and still more preferably 1.0 or less. It is preferred that the difference between a surface friction coefficient ratio Qb and a surface friction coefficient ratio Qa tends to decrease since a difference between lubricity when the medical device is applied to the living body and lubricity before application (for example, upon opening) tends to decrease.

From the viewpoint of supply of oxygen from atmospheric air to body tissues (eye in the case of a lens for eye) of the patient, the medical device of the present invention preferably has high oxygen permeability. The oxygen permeability [$\times 10^{-11}$ (cm$^2$/sec) mLO$_2$/(mL·hPa)] is preferably from 50 to 2,000, more preferably from 100 to 1,500, still more preferably from 200 to 1,000, and most preferably from 300 to 700. It is not preferred that the oxygen permeability is excessively increased since an adverse influence may be sometimes exerted on other physical properties such as mechanical properties. The oxygen permeability is measured using a specimen in a dry state.

In the medical device of the present invention, shape recovery properties, for example, zero-stress time is preferably 1.00 seconds or less, more preferably 0.90 second or less, and most more preferably 0.83 second or less. The zero-stress time is measured by the method disclosed in Examples, using samples in a state of being wetted with a borate buffer.

Anti-fouling property of the medical device of the present invention can be evaluated by adhesion of mucin, adhesion of lipid (methyl palmitate), and an artificial lacrimal fluid immersion test. The amount of adhesion determined by these evaluations is preferably as small as possible since the medical device is excellent in comfort, and also a risk of the growth of bacteria is reduced. The amount of adhesion of mucin is preferably 5 μg/cm$^2$ or less, more preferably 4 μg/cm$^2$ or less, and most preferably 3 μg/cm$^2$ or less.

The medical device of the present invention contains a lens-shaped or sheet-shaped molding (hereinafter referred to as a base material) according to the intended uses, and a layer made of an acidic polymer and a basic polymer is formed on at least a part of a surface of the base material.

The base material contains, as a main component, a copolymer containing a monofunctional monomer component M having one polymerizable functional group and one silicone moiety per molecule Hereinafter, "a monofunctional monomer having one polymerizable functional group and one silicone moiety per molecule component M" is referred to as a "component M". As used herein, the main component means a component which is contained in the amount of 50% by mass or more based on the mass of the base material in a dry state (100% by mass). The copolymer containing a component M means a copolymer obtained by polymerizing a component M and other monomers.

As used herein, the silicone moiety means an organic group having at least one Si—O—Si bond (siloxane bond). The silicone moiety of the component M is preferably linear. When the silicone moiety is linear, shape recovery properties of the obtained medical device are improved. As used herein, linear structure refers to a structure indicated by one linear descrete Si—(O—Si)$_{n-1}$—O—Si bond (provided that n represents an integer of 2 or more) with silicon atoms bonded to a group having a polymerizable group as a starting point. In order that the obtained medical device obtains sufficient shape recovery properties, n is preferably an integer of 3 or more, more preferably 4 or more, still more preferably 5 or more, and most preferably 6 or more. The phrase "the silicone moiety is linear" means that the silicone moiety has the linear structure, and is also free from a Si—O—Si bond which does not satisfy the conditions of the linear structure.

Number average molecular weight of the component M is preferably from 300 to 120,000. When the number average molecular weight of the component M is within the above range, it is possible to obtain a base material, which is flexible and is excellent in comfort, and is also excellent in mechanical properties such as folding resistance. Number average molecular weight of the component M is more preferably 500 or more since it is possible to obtain a base material which is excellent in mechanical properties such as folding resistance and is also excellent in shape recovery properties. The number average molecular weight of the component M is more preferably within a range from 1,000 to 25,000, and still more preferably from 5,000 to 15,000. When the number average molecular weight of the component M is too small, mechanical properties such as folding resistance and shape recovery properties may deteriorate. In particular, when the number average molecular weight is less than 500, folding resistance and shape recovery properties may deteriorate. It is not preferred that the number average molecular weight of the component M is too large since flexibility and transparency may deteriorate.

In the present invention, number average molecular weight of the component M is polystyrene-equivalent number average molecular weight to be measured by a gel permeation chromatographic method (GPC method) using chloroform as a solvent. Mass average molecular weight and dispersion degree (value obtained by dividing mass average molecular weight by number average molecular weight) are also measured by a similar method. Regarding other components used as the base material of the present invention, number average molecular weight and mass average molecular weight are measured by the similar method.

As used herein, the mass average molecular weight is sometimes represented by Mw, and the number average molecular weight is sometimes represented by Mn. The molecular weight of 1,000 is sometimes written as 1 kD. For example, the notation "Mw 33 kD" means "mass average molecular weight of 33,000".

The polymerizable functional group of the component M is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

As used herein, the term "(meth)acryloyl" represents both methacryloyl and acryloyl, and the same shall apply to terms such as (meth)acryl and (meth)acrylate.

The component M preferably has a structure of the following formula (M1).

[Chemical Formula 2]

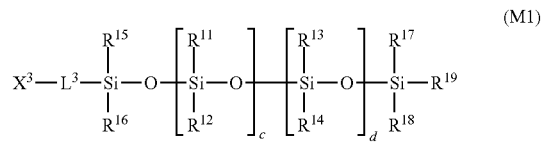

In the formula, $X^3$ represents a polymerizable functional group. $R^{11}$ to $R^{19}$ each independently represents a substituent selected from hydrogen, an alkyl group having 1 to 20 carbon atoms, a phenyl group, and a fluoroalkyl group having 1 to 20 carbon atoms. $L^3$ represents a divalent group. c and d each independently represents an integer of 0 to 700, provided that c and d are not simultaneously 0.

$X^3$ is preferably the above-mentioned radical polymerizable functional group.

Suitable Examples of $R^{11}$ to $R^{19}$ include hydrogen; an alkyl group having 1 to 20 carbon atoms, such as a methyl group, an ethyl group, a propyl group, an isopropyl group, a butyl group, a t-butyl group, a decyl group, a dodecyl group, or an octadecyl group; a phenyl group; and a fluoroalkyl group having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. Among these groups, from the viewpoint of imparting satisfactory mechanical properties and high oxygen permeability to a medical device, hydrogen and a methyl group are preferable, and a methyl group is most preferable.

$L^3$ is preferably a divalent group having 1 to 20 carbon atoms. Among these groups, groups represented by the following formulas (LE1) to (LE12) are preferable since a compound of the formula (M1) has an advantage of easily obtaining with high purity. Among these, $L^3$ are more preferably groups represented by the formulas (LE1), (LE3), (LE9) and (LE11) shown below, still more preferably groups represented by the formulas (LE1) and (LE3) shown below, and most preferably a group represented by the formula (LE1) shown below. In the formulas (LE1) to (LE12) shown below, left side is drawn as an end which is bonded to a polymerizable functional group $X^3$, while right side is drawn as an end which is bonded to a silicon atom.

[Chemical Formula 3]

| | |
|---|---|
| $OCH_2CH_2CH_2$ | (LE1) |
| $NHCH_2CH_2CH_2$ | (LE2) |
| $OCH_2CH_2NHCOOCH_2CH_2CH_2$ | (LE3) |
| $OCH_2CH_2NHCONHCH_2CH_2CH_2$ | (LE4) |
| $OCH_2CH_2CH_2CH_2$ | (LE5) |
| $NHCH_2CH_2CH_2CH_2$ | (LE6) |
| $OCH_2CH_2NHCOOCH_2CH_2CH_2CH_2$ | (LE7) |
| $OCH_2CH_2NHCONHCH_2CH_2CH_2CH_2$ | (LE8) |
| $OCH_2CH_2OCH_2CH_2CH_2$ | (LE9) |
| $NHCH_2CH_2OCH_2CH_2CH_2$ | (LE10) |
| $OCH_2CH_2NHCOOCH_2CH_2OCH_2CH_2CH_2$ | (LE11) |
| $OCH_2CH_2NHCONHCH_2CH_2OCH_2CH_2CH_2$ | (LE12) |

In the formula (M1), c and d each independently represents an integer of 0 to 700, provided that c and d are not simultaneously 0. The total value of c and d (c+d) is preferably 3 or more, more preferably 10 or more, still preferably from 10 to 500, even more preferably from 30 to 300, and yet more preferably from 50 to 200.

When all of $R^{11}$ to $R^{18}$ are methyl groups, d=0, and c is preferably from 3 to 700, more preferably from 10 to 500, still more preferably from 30 to 300, and even more preferably from 50 to 200. In this case, the value of c is determined by the molecular weight of the component M.

In the base material of the medical device of the present invention, the component M of the present invention may be used alone, or two or more kinds may be used in combination.

As a preferred aspect of the medical device of the present invention, the base material preferably contains, as a main component, a polymer having the component M and a polysiloxane compound having a plurality of polymerizable functional groups per molecule and a number average molecular weight of 6,000 or more as a component A.

As used herein, polysiloxane compound represents a compound having a repeating structure (r) represented by:

[Chemical Formula 4]

($R^a$ and $R^b$ are monovalent organic groups, and the repeating structure (r) may be a combination of $R^a$ and $R^b$ which are the same or different).

The component A is a polysiloxane compound having plurality of polymerizable functional groups, and the number of polymerizable functional groups of the component A may be 2 or more per molecule and is preferably 2 per molecule from the viewpoint of easily obtaining a more flexible (low elastic modulus) medical device. The component A may have a polymerizable functional group at any position of a molecular chain, and particularly preferably has a structure having a polymerizable functional group at both ends of the molecular chain.

The component A preferably has a number average molecular weight of 6,000 or more. When the number average molecular weight of the component A is within the above range, it is possible to obtain a medical device which is flexible and is therefore excellent in comfort, and is also excellent in mechanical properties such as folding resistance. The number average molecular weight of the polysiloxane compound as the component A is preferably 8,000 or more since it is possible to obtain a medical device which is excellent in mechanical properties such as folding resistance. The number average molecular weight of the component A is preferably within a range from 8,000 to 100,000, more preferably from 9,000 to 70,000, and still more preferably from 10,000 to 50,000. When the number average molecular weight of the component A is too small, mechanical properties such as folding resistance may deteriorate. When the number average molecular weight of the component A is less than 6,000, folding resistance may deteriorate. It is not preferred that the number average molecular weight of the component A is too large since flexibility and transparency may deteriorate.

It is preferred that the medical device has high transparency when used for a low water content soft lens for eye. Regarding criteria of transparency, it is preferred that the medical device is transparent with no turbidity when visually observed. Furthermore, when the lens for eye is observed by a lens projector, it is preferred that turbidity is scarcely or not observed, and it is most preferred that no turbidity is observed.

Dispersion degree (value obtained by dividing mass average molecular weight by number average molecular weight) of the component A is preferably 6 or less, more preferably 3 or less, still more preferably 2 or less, and most preferably 1.5 or less. When the dispersion degree of the component A is low, it is possible to achieve such benefits that compatibility with other components is improved and thus transparency of the obtained medical device is improved; extractable components contained in the obtained medical device; and a ratio of shrinkage associated with medical device molding decreases. When the medical device is a lens for eye, the ratio of shrinkage associated with lens molding can be evaluated by a molding ratio of lens=[diameter of lens]/[diameter of cavity portion of mold]. As the molding ratio of lens approaches 1, it becomes easier to stably produce a high-quality lens. The molding ratio is preferably within a range from 0.85 to 2.0, more preferably from 0.9 to 1.5, and most preferably from 0.91 to 1.3.

The polymerizable functional group of the component A is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability. When the component A has two or more polymerizable functional groups in the molecule, polymerizable functional groups contained in the molecule may be the same or different polymerizable functional group.

The polymerizable functional group of the component A is more preferably copolymerizable with the polymerizable functional group of the component M since a medical device having satisfactory mechanical properties is easily obtainable. The polymerizable functional group of the component A is more preferably identical to the polymerizable functional group of the component M since a medical device having satisfactory surface properties is easily obtainable by uniformly copolymerizing the component M with the component A. Most preferably, both the polymerizable functional group of the component A and the polymerizable functional group of the component M are (meth)acryloyl groups.

The component A preferably has a structure of the following formula (A1).

[Chemical Formula 5]

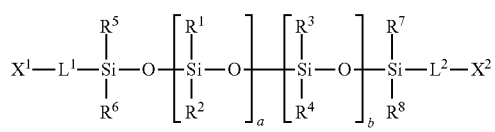

(A1)

In the formula (A1), $X^1$ and $X^2$ each independently represents a polymerizable functional group. $R^1$ to $R^8$ each independently represents a substituent selected from hydrogen, an alkyl group having 1 to 20 carbon atoms, a phenyl group, and a fluoroalkyl group having 1 to 20 carbon atoms. $L^1$ and $L^2$ each independently represents a divalent group. a and b each independently represents an integer of 0 to 1,500, provided that a and b are not simultaneously 0.

$X^1$ and $X^2$ are preferably radical polymerizable functional groups, and radical polymerizable functional groups having a carbon-carbon double bond are preferable. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

Suitable specific examples of $R^1$ to $R^8$ include hydrogen; an alkyl group having 1 to 20 carbon atoms, such as a methyl group, an ethyl group, a propyl group, an isopropyl group, a butyl group, a t-butyl group, a decyl group, a dodecyl group, or an octadecyl group; a phenyl group; and a fluoroalkyl group having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, or a nonadecafluorodecyl group. Among these groups, hydrogen and a methyl group are more preferable from the viewpoint of imparting satisfactory mechanical properties and high oxygen permeability to the medical device, and a methyl group is most preferable.

$L^1$ and $L^2$ are preferably divalent groups having 1 to 20 carbon atoms. Among these groups, groups represented by the following formulas (LE1) to (LE12) are preferable since a compound of the formula (A1) has an advantage of easily obtaining with high purity. Among these, $L^1$ and $L^2$ are more preferably groups represented by the following formulas (LE1), (LE3), (LE9) and (LE11), still more preferably groups represented by the following formulas (LE1) and (LE3), and most preferably a group represented by the following formula (LE1). In the following formulas (LE1) to (LE12), left side is drawn as an end which is bonded to a polymerizable functional group $X^1$ or $X^2$, while right side is drawn as an end which is bonded to a silicon atom.

[Chemical Formula 6]

OCH$_2$CH$_2$CH$_2$                                  (LE1)

NHCH$_2$CH$_2$CH$_2$                              (LE2)

OCH$_2$CH$_2$NHCOOCH$_2$CH$_2$CH$_2$       (LE3)

OCH$_2$CH$_2$NHCONHCH$_2$CH$_2$CH$_2$     (LE4)

OCH$_2$CH$_2$CH$_2$CH$_2$                            (LE5)

NHCH$_2$CH$_2$CH$_2$CH$_2$                          (LE6)

OCH₂CH₂NHCOOCH₂CH₂CH₂CH₂ (LE7)

OCH₂CH₂NHCONHCH₂CH₂CH₂CH₂ (LE8)

OCH₂CH₂OCH₂CH₂CH₂ (LE9)

NHCH₂CH₂OCH₂CH₂CH₂ (LE10)

OCH₂CH₂NHCOOCH₂CH₂OCH₂CH₂CH₂ (LE11)

OCH₂CH₂NHCONHCH₂CH₂OCH₂CH₂CH₂ (LE12)

In the formula (A1), a and b each independently represents an integer of 0 to 1,500, provided that a and b are not simultaneously 0. The total value of a and b (a+b) is preferably 80 or more, more preferably 100 or more, still more preferably from 100 to 1,400, even more preferably from 120 to 950, and yet more preferably from 130 to 700.

When all of $R^1$ to $R^8$ are methyl groups, b=0, and a is preferably from 80 to 1,500, more preferably from 100 to 1,400, still more preferably from 120 to 950, and even more preferably from 130 to 700. In this case, the value of a is determined by the molecular weight of the polysiloxane compound as the component A.

The component A of the present invention may be used alone, or two or more kinds may be used in combination.

In the base material of the medical device of the present invention, regarding a mass ratio of the component M and the component A, the content of the component M is preferably from 5 to 200 parts by mass, more preferably from 7 to 150 parts by mass, and most preferably from 10 to 100 parts by mass, based on 100 parts by mass of the component A. When the base material of the medical device of the present invention contains an appropriate amount of the component M, crosslinking density may decrease leading to an increase in the degree of freedom of a polymer, thus enabling realization of a base material having moderately flexible low elastic modulus. In contrast, when the content of the component M is less than 5 parts by mass based on 100 parts by mass of the component A, crosslinking density may increase leading to a hard base material. When the content of the component M is more than 200 parts by mass based on 100 parts by mass of the component A, the base material may become too soft and thus it is likely to be broken, and thus both cases are not preferred.

As another preferred aspect of the medical device of the present invention, the base material preferably contains, as a main component, a copolymer containing the component M, the component A, and a polymerizable monomer having a fluoroalkyl group as a component B.

The component B has properties of water and oil repellency due to a decrease in critical surface tension caused by a fluoroalkyl group, thereby exerting the effect of suppressing a surface of a mechanical device from being contaminated with components such as protein and lipid in a lacrimal fluid. The component B also has the effect of giving a medical device, which is flexible and is excellent in comfort, and is also excellent in mechanical properties such as folding resistance. Suitable specific examples of the fluoroalkyl group of the component B include fluoroalkyl groups having 1 to 20 carbon atoms, such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. The fluoroalkyl group is more preferably a fluoroalkyl group having 2 to 8 carbon atoms, for example, a trifluoroethyl group, a tetrafluoropropyl group, a hexafluoroisopropyl group, an octafluoropentyl group or a dodecafluorooctyl group, and most preferably a trifluoroethyl group.

The polymerizable functional group of the component B is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, a citraconic acid residue and the like. Among these polymerizable functional groups, a (meth)acryloyl group is most preferable since it has high polymerizability.

A (meth)acrylic acid fluoroalkyl ester is most preferably as the component B since it has significant effect of giving a medical device, which is flexible and is excellent in comfort, and is also excellent in mechanical properties such as folding resistance. Specific examples of the (meth)acrylic acid fluoroalkyl ester include trifluoroethyl (meth)acrylate, tetrafluoroethyl (meth)acrylate, trifluoropropyl(meth)acrylate, tetrafluoropropyl (meth)acrylate, pentafluoropropyl (meth)acrylate, hexafluorobutyl (meth)acrylate, hexafluoroisopropyl (meth)acrylate, heptafluorobutyl (meth)acrylate, octafluoropentyl (meth)acrylate, nonafluoropentyl (meth)acrylate, dodecafluoroheptyl (meth)acrylate, dodecafluoroheptyl (meth)acrylate, dodecafluorooctyl (meth)acrylate, and tridecafluoroheptyl (meth)acrylate. Trifluoroethyl (meth)acrylate, tetrafluoroethyl (meth)acrylate, hexafluoroisopropyl (meth)acrylate, octafluoropentyl (meth)acrylate, and dodecafluorooctyl (meth)acrylate are preferably used. Trifluoroethyl (meth)acrylate is most preferable. The component B of the present invention may be used alone, or two or more kinds may be used in combination.

The content of the component B in the copolymer is preferably from 10 to 500 parts by mass, more preferably from 20 to 400 parts by mass, and still more preferably from 20 to 200 parts by mass, based on 100 parts by mass of the component A. When the use amount of the component B is too small, white turbidity may arise in the base material, or mechanical properties such as folding resistance may become insufficient.

It is possible to use, as the copolymer to be used in the base material, a copolymer obtained by copolymerizing a component which is different from the components M, A and B (hereinafter referred to as a component C), in addition to the components M, A and B.

The component C may be a component which decreases a glass transition point of a copolymer to room temperature, or 0° C. or lower. The component decreases cohesive energy and therefore exerts the effect of imparting rubber elasticity and flexibility to the copolymer.

The polymerizable functional group as the component C is preferably a radical polymerizable functional group, and more preferably a radical polymerizable functional group having a carbon-carbon double bond. Examples of preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residue, an isocrotonic acid residue, and a citraconic acid residue. Among these polymerizable functional groups, a (meth) acryloyl group is most preferable since it has high polymerizability.

The component C, which is suitable for the improvement of mechanical properties such as flexibility and folding resistance, is a (meth)acrylic acid alkyl ester, and preferably a (meth)acrylic acid alkyl ester whose alkyl group has 1 to 20 carbon atoms, and specific examples thereof include methyl (meth)acrylate, ethyl (meth)acrylate, n-propyl (meth)acrylate, n-butyl (meth)acrylate, tert-butyl (meth) acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth) acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, n-stearyl (meth)acrylate and the like. The (meth)acrylic acid alkyl ester is more preferably n-butyl (meth)acrylate, n-octyl (meth)acrylate, n-lauryl (meth)acrylate, or n-stearyl (meth) acrylate. Among these, a (meth)acrylic acid alkyl ester whose alkyl group has 1 to 10 carbon atoms is more preferable. It is not preferred that the number of carbon atoms of the alkyl group is too large since transparency of the obtained medical device may sometimes deteriorate.

Furthermore, in order to improve mechanical properties, surface wettability, dimensional stability of the medical device and the like, the below-mentioned monomer can be optionally copolymerized as the component C.

Examples of the monomer for the improvement of mechanical properties include an aromatic vinyl compound such as styrene, tert-butylstyrene, or α-methylstyrene.

Examples of the monomer for the improvement of surface wettability include methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N-dimethylacrylamide, N-methylacrylamide, N,N-dimethylaminoethyl methacrylate, methylenebisacrylamide, diacetoneacrylamide, N-vinylpyrrolidone, N-vinylcaprolactam, N-vinylacetamide, N-vinyl-N-methylacetamide and the like. Among these monomers, a monomer having an amide group or an amine group, such as N,N-dimethylacrylamide, N-methylacrylamide, N,N-dimethylaminoethyl methacrylate, methylenebisacrylamide, diacetoneacrylamide, N-vinylpyrrolidone, N-vinylcaprolactam, N-vinylacetamide, or N-vinyl-N-methylacetamide is preferable. A monomer having an amino group, such as N,N-dimethylaminoethyl methacrylate is particularly suitable because of its satisfactory compatibility with a pigment.

Examples of the monomer for the improvement of dimensional stability of the medical device include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate, and acrylates corresponding to these methacrylates, divinylbenzene, triallyl isocyanurate and the like.

In the base material of medical device of the present invention, the component C may be used alone, or two or more kinds may be used in combination.

The use amount of the component C is preferably from 0.001 to 400 parts by mass, more preferably from 0.01 to 300 parts by mass, still more preferably from 0.01 to 200 parts by mass, and most preferably from 0.01 to 30 parts by mass, based on 100 parts by mass of the component A. When the use amount of the component C is too small, it may become difficult to obtain the effect which is expected to the component C. When the use amount of the component C is too large, white turbidity may arise in the obtained medical device, or mechanical properties such as folding resistance may become insufficient.

The medical device of the present invention may further contain a component (component Ck) such as an ultraviolet absorber, a pigment, a colorant, a humectant, a slip agent, a pharmaceutical and a nutritional supplementary component, a compatibilizing component, an antibacterial component, a mold release agent and the like. Any of the above-mentioned components can be contained in a non-reactive form or a copolymerization form.

In the case of using the component Ck, the use amount of the component Ck is preferably from 0.00001 to 100 parts by mass, more preferably from 0.0001 to 30 parts by mass, and still more preferably from 0.0001 to 10 parts by mass, based on 100 parts by mass of the component A. When the use amount of the component Ck is too small, it may be impossible to sufficiently obtain the effect of the ultraviolet absorber and the colorant to the component. It is not preferred that the use amount of the component Ck is too large since white turbidity may arise in the medical device.

When the base material of the medical device of the present invention contains an ultraviolet absorber, it is possible to protect body tissue (eye in the case of a lens for eye) of wearers using a medical device from harmful ultraviolet rays. In the case of containing a colorant, the medical device is colored, results in easy identification and an improvement in convenience during handling.

Any of the above-mentioned components can be contained in a non-reactive form or a copolymerization form. It is preferred that the above components are copolymerized, that is, an ultraviolet absorber having a polymerizable group or a colorant having a polymerizable group is used since the component is copolymerized with a base material and immobilized, and thus elution may scarcely occur.

In a form of the base material of the medical device according to the present invention, it is preferred to contain, as copolymerization components, a component selected from an ultraviolet absorber and a colorant (component Ck), two or more kinds of components C, M, A and B. In that case, it is preferred that at least one is elected from a (meth)acrylic acid alkyl ester having 1 to 10 carbon atoms, and at least one is selected from a monomer for the improvement of surface wettability, as the component C. Use of two or more kinds of components C enhances affinity with an ultraviolet absorber or a colorant, and thus it becomes possible to obtain a transparent base material.

In the case of using an ultraviolet absorber, the use amount thereof is preferably from 0.01 to 20 parts by mass, more preferably from 0.05 to 10 parts by mass, and still more preferably from 0.1 to 2 parts by mass, based on 100 parts by mass of the component A. In the case of using a colorant, the use amount thereof is preferably from 0.00001 to 5 parts by mass, more preferably from 0.0001 to 1 part by mass, and still more preferably from 0.0001 to 0.5 part by mass, based on 100 parts by mass of the component A. When the content of the ultraviolet absorber or colorant is too small, it may become difficult to obtain the ultraviolet absorption effect or coloration effect. In contrast, when the content is too large, it may become difficult to dissolve these components in the base material.

Crosslinking degree of the base material of the medical device of the present invention, obtained by copolymerizing the component selected from the above-mentioned components, is preferably within a range from 2.0 to 18.3. The crosslinking degree is represented by the following equation (Q1).

[Equation 1]

$$\text{Crosslinking degree} = \frac{\sum_{n=1}^{\infty} \{Qn \times (n-1)\}}{\sum_{n=1}^{\infty} Wn} \quad (Q1)$$

In the formula (Q1), Qn represents a total millimolar amount of a monomer having n polymerizable groups per molecule, and Wn represents a total mass (kg) of a monomer having n polymerizable groups per molecule. When molecular weight of the monomer has distribution, the millimolar amount is calculated using number average molecular weight.

It is not preferred that the crosslinking degree of the base material of the present invention is less than 2.0 since it may become difficult to handle because of being too soft. It is not preferred that the crosslinking degree of the base material is more than 18.3 since comfort may become worse because of being too hard. The crosslinking degree is more preferably within a range from 3.5 to 16.0, still more preferably from 8.0 to 15.0, and most preferably from 9.0 to 14.0.

The base material preferably contains 5% by mass or more of silicon atoms in order to have high oxygen permeability, and to obtain strong adhesion with a polymer to be coated on a surface without involving in a covalent bond. The content (% by mass) of silicon atoms is calculated based on the mass of the base material in a dry state (100% by mass). The content of silicon atoms of the base material is preferably from 5% by mass to 36% by mass, more preferably from 7% by mass to 30% by mass, still more preferably from 10% by mass to 30% by mass, and most preferably 12% by mass to 26% by mass. It is not preferred that the content of silicon atoms is too large since tensile elastic modulus may sometimes increase.

The content of silicon atoms in the base material can be measured by the following method. After weighing sufficiently dried base material in a platinum crucible, sulfuric acid is added then the base material is incinerated by heating using a hotplate and a burner. The obtained ash is melted with sodium carbonate and water is added. After dissolving by heating, nitric acid is added and the volume is fixed by water. Regarding this solution, silicon atoms are measured by ICP emission spectrometry and the content in the base material is determined.

It is possible to use, as a method for producing a base material of a medical device, namely, a lens-shaped or sheet-shaped molding, a known method. For example, it is possible to use a method in which a round bar- or plate-shaped polymer is once obtained and then processed into a desired shape by cutting or the like, a mold polymerization method, a spin-cast polymerization method and the like. In the case of obtaining a medical device by cutting, freeze-cutting at low temperature is suitable.

A method of polymerizing a raw material composition containing a component M by a mold polymerization method to produce a lens for eye will be described below as an example. First, a gap between two mold members each having a fixed shape is filled with a raw material composition. Examples of the material of the mold member include resin, glass, ceramics, metal and the like. In the case of performing photopolymerization, since an optically transparent material is preferable, the resin or glass is preferably used. Depending on the shape of the mold member or properties of the raw material composition, a gasket may be used so as to impart a fixed thickness to the lens for eye, and to prevent liquid leakage of the raw material composition filled in the gap. The mold with the gap filled with raw material composition is subsequently irradiated with active rays such as ultraviolet rays, visible rays or a combination thereof, or heating in an oven or a liquid bath, thereby polymerizing the raw material composition filled in the mold. It is also possible to employ a method using two types of polymerization methods. That is, it is also possible to perform heat polymerization after photopolymerization, or perform photopolymerization after heat polymerization. In a specific aspect of photopolymerization, for example, light including ultraviolet rays such as light of a mercury lamp or an ultraviolet lamp (for example, FL15BL, Toshiba Corporation) are irradiated within a short time (usually 1 hour or less). In the case of performing heat polymerization, conditions of gradually raising a temperature of the composition from about room temperature and raising to the temperature of 60° C. to 200° C. over several hours to several tens of hours are preferably used so as to maintain optical uniformity and grade of a lens for eye, and to enhance reproducibility.

In the polymerization, a heat polymerization initiator typified by a peroxide or an azo compound, or a photopolymerization initiator is preferably added so as to facilitate the polymerization. In the case of performing heat polymerization, an initiator having optimum decomposition characteristics at a desired reaction temperature is selected. Commonly, an azo-based initiator and a peroxide-based initiator, each having a ten-hour half-life temperature of 40 to 120° C., are suitable. Examples of the photoinitiator in the case of performing photopolymerization include a carbonyl compound, a peroxide, an azo compound, a sulfur compound, a halogen compound, a metal salt and the like. These polymerization initiators are used alone or in combination. The amount of the polymerization initiator is preferably up to 5% by mass based on a polymerization mixture.

In the case of performing polymerization, a polymerization solvent can be used. Organic and inorganic various solvents can be applied as the solvent. Examples of the solvent include water; alcohol-based solvents such as methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, and tetraethylene glycol and polyethylene glycol; glycol ether-based solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester-based solvents such as ethyl acetate, butyl acetate, amyl acetate, ethyl lactate, and methyl benzoate; aliphatic hydrocarbon-based solvents such as normal hexane, normal heptane, and normal octane; alicyclic hydrocarbon-based solvents such as cyclohexane and ethylcyclohexane; ketone-based solvents such as acetone, methyl ethyl ketone, and methyl isobutyl ketone; aromatic hydrocarbon-based solvents such as benzene, toluene, and xylene; and petroleum-based solvents. These solvents may be used alone, or two or more kinds may be used in combination.

It is required that a layer made of an acidic polymer and a basic polymer (hereinafter referred to as a coating layer) is formed on at least a part of a surface of a base material in the medical device of the present invention. Inclusion of a coating layer imparts satisfactory wettability and lubricity to the surface of the medical device, and thus imparting excellent comfort.

The present inventors have found that, even if the medical device of the present invention has low water content and is soft, and also the base material is neutral, it is possible to impart sufficient wettability, lubricity and anti-fouling property to the surface of the medical device by forming a coating layer made of an acidic polymer and a basic polymer on the surface. Thereby, according to the medical device of the present invention, it is possible to significantly reduce or avoid a phenomenon of adhesion to the cornea during wear, which has hitherto been regarded as a problem in a low water content soft lens for eye as an example of intended uses of a conventional medical device.

It is not necessary to have a covalent bond between the coating layer and the base material. It is preferred to have no covalent bond between the coating layer and the base material since it become possible to produce by a simple and easy step. The coating layer has practical durability even in the case of having no covalent bond between the coating layer and the base material.

The coating layer is formed by treating a surface of a base material with an acidic polymer solution ("solution" means an aqueous solution) and a basic polymer solution ("solution" means an aqueous solution) which will be described in detail below. The aqueous solution means a solution containing water as a main component.

The coating layer is preferably made of one or more kinds of acidic polymers and one or more kinds of basic polymers. Use of two or more kinds of acidic polymers or two or more kinds of basic polymers are more preferable since it is easy to develop properties such as lubricity and anti-fouling property to the surface of the medical device. In particular, use of two or more kinds of acidic polymers and one or more kinds of basic polymers are more preferable since this tendency is to be further increased.

The coating layer is preferably formed by performing a treatment with one or more kinds of acidic polymer solutions one or more times, and a treatment with one or more kinds of basic polymer solutions one or more times.

The coating layer is preferably formed on a surface of the base material by the treatment with one or more kinds of acidic polymer solutions and the treatment with one or more kinds of basic polymer solutions 1 to 5 times, more preferably 1 to 3 times, and still more preferably 1 to 2 times, respectively. The number of times of the treatment with an acidic polymer solution may be different from the number of times of the treatment with a basic polymer solution.

In the medical device of the present invention, it is possible to impart excellent wettability and lubricity by performing the treatment with an acidic polymer solutions and the treatment with a basic polymer solutions very small number of times (2 or 3 in total) in the medical device of the present invention. This fact is crucially important for industry from the viewpoint of shortening of the production process. In that sense, the coating layer is preferably formed by performing the treatment with an acidic polymer solution once or twice, and the treatment with a basic polymer solution once or twice, that is, two or three times in total.

The coating layer is preferably formed by performing the treatment with one or more kinds of acidic polymer solutions twice, and the treatment with a basic polymer solution once, and particularly preferably formed by performing t the treatment with two kinds of acidic polymer solutions (each once), and the treatment with a basic polymer solution once, that is, three times in total.

Therefore, in the medical device of one of preferred aspects of the present invention, the coating layer is formed of one kind of an acidic polymer and one kind of a basic polymer.

In one of other preferred aspects of the medical device of the present invention, the coating layer is formed of two kinds of acidic polymers and one kind of a basic polymer.

The present inventors have also confirmed that wettability and lubricity are scarcely developed only by containing either an acidic polymer solution or a basic polymer solution in the coating layer.

It is possible to suitably use, as the basic polymer, a homopolymer or copolymer having a plurality of groups having basicity along a polymer chain. An amino group and salts thereof are suitable as the group having basicity. Suitable examples of the basic polymer include an amino group-containing (meth)acrylate polymer such as poly(allylamine), poly(vinylamine), poly(ethyleneimine), poly(vinylbenzyltrimethylamine), polyaniline, poly(aminostyrene), or poly(N,N-dialkylaminoethyl methacrylate); an amino group-containing (meth)acrylamide polymer such as poly (N,N-dimethylaminopropylacrylamide); and salts thereof. Although the above basic polymers are examples of a homopolymer, these copolymers (i.e., a copolymer of basic monomers each composing the basic polymer, or a copolymer of a basic monomer and the other monomer) can also be suitably used.

When the basic polymer is a copolymer, the basic monomer composing the copolymer is preferably a monomer having an allyl group, a vinyl group, and a (meth)acryloyl group from the viewpoint of high polymerizability, and most preferably a monomer having a (meth)acryloyl group. Suitable examples of the basic monomer composing the copolymer include allylamine, vinylamine (N-vinylcarboxylic acid amide as a precursor), vinylbenzyltrimethylamine, amino group-containing styrene, amino group-containing (meth)acrylate, amino group-containing (meth)acrylamide, and salts thereof. Among these monomers, amino group-containing (meth)acrylate, amino group-containing (meth) acrylamide, and salts thereof are more preferably from the viewpoint of high polymerizability, and N,N-dimethylaminoethyl methacrylate, N,N-dimethylaminopropyl acrylamide, and salts thereof are most preferable.

The basic polymer may be a polymer having a quaternary ammonium structure. The polymer having a quaternary ammonium structure compound can impart antimicrobial properties to a medical device when used for coating of the medical device.

It is possible to suitably use, as the acidic polymer, a homopolymer or copolymer having a plurality of groups having acidity along a polymer chain. The group having acidity is suitably a carboxyl group, a sulfonic acid group and salts thereof, and most suitably a carboxyl group, and salts thereof. Examples of suitable acidic polymer include polymethacrylic acid, polyacrylic acid, poly(vinylbenzoic acid), poly(thiophene-3-acetic acid), poly(4-styrenesulfonic acid), polyvinylsulfonic acid, poly(2-acrylamide-2-methylpropanesulfonic acid), and salts thereof. Although the above polymers are examples of a homopolymer, these copolymers (i.e., a copolymer of acidic monomers composing the acidic polymer, or a copolymer of an acidic monomer and the other monomer) can also be suitably used.

When the acidic polymer is a copolymer, the acidic monomer composing the copolymer is preferably a monomer having an allyl group, a vinyl group, and a (meth)acryloyl group from the viewpoint of high polymerizability, and most preferably a monomer having a (meth)acryloyl group. Suitable examples of the acidic monomer composing the copolymer include (meth)acrylic acid, vinylbenzoic acid, styrenesulfonic acid, vinylsulfonic acid, 2-acrylamide-2-methylpropanesulfonic acid, and salts thereof. Among these monomers, (meth)acrylic acid, 2-acrylamide-2-methylpropanesulfonic acid, and salts thereof are more preferable, and (meth)acrylic acid, and salts thereof are most preferable.

It is preferred that at least one of basic and acidic polymers is a polymer having a group selected from an amide group and a hydroxyl group, in addition to a group having basicity or a group having acidity. It is preferred that a basic polymer and/or an acidic polymer has/have an amide group since a surface having not only wettability but also lubricity can be formed. It is preferred that a basic polymer and/or an acidic polymer has/have a hydroxyl group since a surface having not only excellent wettability but also excellent anti-fouling property against a lacrimal fluid can be formed.

It is more preferred that a polymer having a group selected from a hydroxyl group and an amide group is used in two or more treatments among two or three treatments (coatings) with the acidic polymer solution and basic polymer solution subjected to the molding. That is, it is preferred that the coating layer of the medical device contains two or more kinds selected from an acidic polymer having a hydroxyl group, a basic polymer having a hydroxyl group, an acidic polymer having an amide group, and a basic polymer having an amide group. In this case, it is preferred since the effect of forming a surface having lubricity, and the effect capable of forming a surface having excellent anti-fouling property against a lacrimal fluid can be exerted more significantly.

It is more preferred that the coating layer contains at least one selected from an acidic polymer having a hydroxyl group and a basic polymer having a hydroxyl group, and at least one selected from an acidic polymer having an amide group, and a basic polymer having an amide group. In this case, it is preferred since both the effect of forming a surface having lubricity, and the effect capable of forming a surface having excellent anti-fouling property against a lacrimal fluid can be exerted.

Examples of the basic polymer having an amide group include polyamides having an amino group, partially hydrolyzed chitosan, a copolymer of a basic monomer and a monomer having an amide group and the like.

Examples of the acidic polymer having an amide group include polyamides having a carboxyl group, a copolymer of an acidic monomer and a monomer having an amide group and the like.

Examples of the basic polymer having a hydroxyl group include aminopolysaccharides such as chitin, a copolymer of a basic monomer and a monomer having a hydroxyl group and the like.

Examples of the acidic polymer having a hydroxyl group include polysaccharides having an acidic group, such as hyaluronic acid, chondroitin sulfate, carboxymethyl cellulose, and carboxypropyl cellulose; a copolymer of an acidic monomer and a monomer having an amide group and the like.

The monomer having an amide group is preferably a monomer having a (meth)acrylamide group and N-vinylcarboxylic acid amide (including a cyclic monomer) from the viewpoint of ease of polymerization. Suitable examples of the monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloylmorpholine, and acrylamide. Among these monomers, N-vinylpyrrolidone and N,N-dimethylacrylamide are preferable from the viewpoint of lubricity, and N,N-dimethylacrylamide is most preferable.

Suitable examples of the monomer having a hydroxyl group include hydroxyethyl (meth)acrylate, hydroxypropyl (meth)acrylate, hydroxybutyl (meth)acrylate, hydroxyethyl (meth)acrylamide, glycerol (meth)acrylate, caprolactone-modified 2-hydroxyethyl (meth)acrylate, N-(4-hydroxyphenyl)maleimide, hydroxystyrene, and vinyl alcohol (carboxylic acid vinyl ester as a precursor). The monomer having a hydroxyl group is preferably a monomer having a (meth)acryloyl group in view of ease of polymerization, and more preferably a (meth)acrylic acid ester monomer. Among these monomers, hydroxyethyl (meth)acrylate, hydroxypropyl (meth)acrylate and glycerol (meth)acrylate are preferable from the viewpoint of anti-fouling property against a lacrimal fluid, and hydroxyethyl (meth)acrylate is most preferable.

Specific examples of preferable copolymer of a basic monomer and a monomer having an amide group include an N,N-dimethylaminoethyl methacrylate/N-vinylpyrrolidone copolymer, an N,N-dimethylaminoethyl methacrylate/N,N-dimethylacrylamide copolymer, N,N-dimethylaminopropylacrylamide/N-vinylpyrrolidone copolymer, and an N,N-dimethylaminopropylacrylamide/N,N-dimethylacrylamide copolymer. An N,N-dimethylaminopropyl acrylamide/N,N-dimethylacrylamide copolymer is more preferable.

Specific examples of preferable copolymer of an acidic monomer and a monomer having an amide group include a (meth)acrylic acid/N-vinylpyrrolidone copolymer, a (meth)acrylic acid/N,N-dimethylacrylamide copolymer, a 2-acrylamide-2-methylpropanesulfonic acid/N-vinylpyrrolidone copolymer, and a 2-acrylamide-2-methylpropanesulfonic acid/N,N-dimethylacrylamide copolymer. A (meth)acrylic acid/N,N-dimethylacrylamide copolymer is most preferable.

Specific examples of preferable copolymer of a basic monomer and a monomer having a hydroxyl group include an N,N-dimethylaminoethyl methacrylate/hydroxyethyl (meth)acrylate copolymer, an N,N-dimethylaminoethyl methacrylate/glycerol (meth)acrylate copolymer, an N,N-dimethylaminopropylacrylamide/hydroxyethyl (meth)acrylate, and an N,N-dimethylaminopropylacrylamide/glycerol (meth)acrylate copolymer. An N,N-dimethylaminoethyl methacrylate/hydroxyethyl (meth)acrylate copolymer is most preferable.

Specific examples of preferable copolymer of an acidic monomer and a monomer having a hydroxyl group include a (meth)acrylic acid/hydroxyethyl (meth)acrylate copolymer, a (meth)acrylic acid/glycerol (meth)acrylate copolymer, a 2-acrylamide-2-methylpropanesulfonic acid/hydroxyethyl (meth)acrylate copolymer, and a 2-acrylamide-2-methylpropanesulfonic acid/glycerol (meth)acrylate copolymer. A (meth)acrylic acid/hydroxyethyl (meth)acrylate copolymer is most preferable.

In the case of using a copolymer of the basic monomer or acidic monomer and the other monomer, the copolymerization ratio [number of mols of basic monomer or acidic monomer]/[number of mols of the other monomer] is preferably from 1/99 to 99/1, more preferably from 2/98 to 90/10, and still more preferably from 10/90 to 80/20. When the copolymerization ratio is within the above range, functions such as lubricity and anti-fouling property against a lacrimal fluid are likely to be developed.

It is possible to use, as the method for producing an acidic polymer and a basic polymer, known methods. For example, monomers are mixed in a solvent in the above-mentioned predetermined ratio and, after adding a polymerization initiator, a polymerization reaction is carried out in the presence of an inert medium at a predetermined temperature while refluxing. The reaction product obtained by the reaction is immersed in a solvent to remove the unreacted monomer components, followed by washing and further drying to obtain a polymer. A homopolymer or di- or higher copolymer can be produced by the above method.

In order to change various characteristics, for example, thickness of the coating layer, it is possible to change molecular weights of an acidic polymer and a basic polymer. Specifically, when the molecular weight is increased, the thickness of the coating layer commonly increases. However, when the molecular weight is too large, it may become difficult to handle due to an increase in viscosity. Therefore, acidic and basic polymers to be used in the present invention preferably have a molecular weight of 2,000 to 150,000. The molecular weight is more preferably from 5,000 to 100,000, and still more preferably from 75,000 to 100,000. The molecular weight of the acidic and basic polymers is a polyethylene glycol-equivalent mass average molecular weight measured by a gel permeation chromatographic method (aqueous solvent).

Coating of the coating layer can be achieved by various methods disclosed, for example, in WO 99/35520, WO 01/57118, or U.S. Patent No. 2001-0045676.

In the medical device of the present invention, a layer made of an acidic polymer and a basic polymer (hereinafter referred to as a coating layer) is formed, while at least a part inside the layer may be crosslinked. In the medical device of the present invention, at least a part may be crosslinked between the base material and the layer. Crosslinking means that polymers are bonded together by forming a crosslinking structure using their own functional group or crosslinking agent.

The above-mentioned crosslinking can be generated by irradiating with radiation in a case where at least an acidic polymer and a basic polymer are adhered to a base material. Radiations are preferably various ion beams, electron beams, positron beams, X-rays, $\gamma$ rays, and neutron beams, more preferably electron beams and $\gamma$ rays, and most preferably $\gamma$ rays.

As mentioned above, satisfactory wettability and lubricity are imparted to a surface of the lens by generating crosslinking inside a coating layer, or the space between a coating layer and a base material, and thus excellent comfort can be imparted. Meanwhile, crosslinking is also generated inside a base material by irradiating with radiation, and thus the medical device may become too hard. In that case, it is possible to suppress excess crosslinking inside the base material by appropriately replacing a component A in the base material by a component M, followed by copolymerization.

The method for producing a medical device of the present invention will be described below. The medical device of the present invention is obtained by coating a surface of a lens-shaped or sheet-shaped molding (base material) with each of one or more kinds of acidic polymer solutions and one or more kinds of basic polymer solutions 1 to 5 times, more preferably 1 to 3 times, and still more preferably 1 to 2 times, to form a coating layer. The number of times of the coating step of an acidic polymer solution may be different from that of the coating step of a basic polymer solution. From the viewpoint of shortening of the production process, the total number of coating steps of acidic and basic polymer solutions is preferably 2 or 3.

The acidic polymer solution and the basic polymer solution are usually solutions containing one kind of a polymer. One kind of a polymer means a polymer group in which the kind of the composing monomer is the same. Even if the kind of the composing monomer is the same, a polymer synthesized by varying a mixing ratio is not one kind. Even in the case of a solution of one kind (same) of a polymer, solutions having different concentrations are not regarded as one kind.

From the viewpoint of wettability, lubricity and shortening of the production process, coating of the coating layer is preferably performed with any constitution selected from the following constitutions 1 to 4. The following notation shows that the respective coating steps are sequentially applied to a surface of a molding from left to right.

Constitution 1: Coating of basic polymer solution/coating of acidic polymer solution Constitution 2: Coating of acidic polymer solution/coating of basic polymer solution Constitution 3: Coating of basic polymer solution/coating of acidic polymer solution/coating of basic polymer solution Constitution 4: Coating of acidic polymer solution/coating of basic polymer solution/coating of acidic polymer solution Among these constitutions, constitutions 1 and 4 are preferable, and constitution 4 is more preferable since the obtained medical device exhibits particularly excellent wettability and shape recovery properties.

In the above constitutions 1 to 4, one or more kinds of basic polymer solutions and/or one or more kinds of acidic polymer solutions can be used. For example, acidic polymer solutions used in an innermost layer and an outermost layer used in the constitution 4 may be the same, or different kinds of acidic polymer solutions may be used.

In the case of coating an acidic polymer solution and a basic polymer solution, a surface of a base material may be untreated or already treated. As used herein, the phrase "surface of a base material is already treated" means that a surface of a base material is subjected to a surface treatment or surface modification by a known method. Suitable examples of the surface treatment or surface modification include a plasma treatment, a chemical modification, a chemical functionalization, a plasma coating and the like.

One of preferred aspects of the method for producing a medical device of the present invention (aspect P1) includes the following steps 1a to 3a in this order:

<Step 1a>

Step of polymerizing a mixture of a component M which is a monofunctional monomer having one polymerizable functional group per molecule, and also having a silicone moiety to obtain a molding;

<Step 2a>

Step of bringing the molding into contact with a basic polymer solution, and then washing the molding to remove the surplus basic polymer solution; and <Step 3a>

Step of bringing the molding into contact with an acidic polymer solution, and then washing the molding to remove the surplus acidic polymer solution;

One of preferred aspects of the method for producing a medical device of the present invention (aspect P2) includes the following steps 1b to 4b in this order:
<Step 1b>
Step of polymerizing a mixture of a component M which is a monofunctional monomer having one polymerizable functional group per molecule, and also having a silicone moiety to obtain a molding;
<Step 2b>
Step of bringing the molding into contact with an acidic polymer solution, and then washing the molding to remove the surplus acidic polymer solution;
<Step 3b>
Step of bringing the molding into contact with a basic polymer solution, and then washing the molding to remove the surplus basic polymer solution; and
<Step 4b>
Step of bringing the molding into contact with an acidic polymer solution, and then washing the molding to remove the surplus acidic polymer solution;

In the step 1a or 1b, the mixture to be polymerized is more preferably a mixture containing a component M which is a monofunctional monomer having one polymerizable functional group per molecule, and also having a silicone moiety, a component A which is a polysiloxane compound having a plurality of polymerizable functional groups per molecule and a number average molecular weight of 6,000 or more, and a component B which is a polymerizable monomer having a fluoroalkyl group.

As mentioned above, a layer made of an acidic polymer and a basic polymer can be formed on a molding by sequentially bringing the molding into contact with an acidic polymer solution and a basic polymer solution. Thereafter, surplus polymer is preferably removed by sufficiently washing.

It is possible to apply, as the method of bringing the molding into contact with an acidic polymer solution or a basic polymer solution, various coating methods such as an immersion method (dipping method), a brush coating method, a spray coating method, a spin coating method, a die coating method and a squeegee method.

When contact with a solution is performed by an immersion method, immersion time can vary depending on various factors. Immersion of a molding in an acidic polymer solution or a basic polymer solution is preferably performed for 1 to 30 minutes, more preferably 2 to 20 minutes, and most preferably 1 to 5 minutes.

The concentration of an acidic polymer solution and a basic polymer solution can vary depending on properties of an acidic polymer or a basic polymer, thickness of a desired coating layer, and other various factors. The concentration of the acidic or basic polymer is from 0.001 to 10% by mass, more preferably from 0.005 to 5% by mass, and most preferably from 0.01 to 3% by mass.

The pH of an acidic polymer solution and a basic polymer solution is preferably maintained within a range from 2 to 5, and more preferably from 2.5 to 4.5.

Removal of surplus acidic polymer and basic polymer by washing is commonly performed by rinsing a molding after coating using clean water or an organic solvent. Rinsing is preferably performed by immersing the molding in water or an organic solvent or exposing to a water flow or an organic solvent flow. Rinsing may be completed in one step. However, it was recognized that it is efficient that a rinsing step is performed plural times. Rinsing is preferably performed in 2 to 5 steps. Immersion of each molding in a rinsing solution is preferably performed for 1 to 3 minutes.

Pure water is also preferably used as the rinsing solution. In order to increase adhesion of a coating layer, it is preferred to use an aqueous buffered solution having pH adjusted within a range from 2 to 7, more preferably from 2 to 5, and still more preferably from 2.5 to 4.5.

In the method for producing a medical device according to the present invention, the step of drying or removing an excess rinsing solution may also be included. A molding can be dried to some extent by merely being left to stand under air atmosphere. Drying is preferably accelerated by supplying a mild air flow to the surface. Flow rate of the air flow can be adjusted as a function of the strength of a material to be dried, and mechanical fixturing of a material. There is no need to completely dry a molding. Herein, it is important to remove droplets of a solution adhered onto a surface of the molding as compared with drying of the molding. Therefore, the molding is only dried until a film of water or a solution on the surface of the molding is removed, leading to shortening of the process time, favorably.

It is preferred that an acidic polymer and a basic polymer are alternately coated. It is possible to obtain a medical device, which has excellent wettability and lubricity that cannot be obtained by any one of these polymers, and also has excellent comfort, by alternately coating the polymers.

The coating layer of medical device of the present invention can be asymmetric. As used herein, "asymmetric" refers to the fact that a coating layer formed on a first side of a medical device is different from that formed on a second side opposite the first side. As used herein, "different coating layers" refer to the fact that a coating layer formed on a first side and a coating layer formed on a second side each has different surface characteristics or functionalities.

The thickness of the coating layer can be controlled by adding one or more salts such as sodium chloride to an acidic polymer solution or a basic polymer solution. The concentration of the salt is preferably from 0.1 to 2.0% by mass. As the concentration of the salt increases, a polyelectrolyte exhibits a more spherical spatial structure. However, when the concentration becomes too high, even if the polyelectrolyte is deposited on a surface of a molding, it is not satisfactorily deposited. More preferably, the concentration of the salt is from 0.7 to 1.3% by mass.

One of other preferred aspects of the method for producing a medical device of the present invention further includes the following step 5;
<Step 5>
Step of forming a layer made of an acidic polymer and a basic polymer on a molding by the above step, and irradiating the molding with radiation.

Irradiation with radiation may be carried out in a state where a molding is immersed in a coating liquid, or may be carried out after pulling up the molding from the coating liquid and further washing. Irradiation with radiation may also be preferably carried out in a state where a molding is immersed in a liquid other than the coating liquid. In this case, it is preferred that radiation efficiently acts. In this case, it is possible to apply, as a solvent for a liquid in which the coated molding is immersed, various organic and inorganic solvents, and there is no particular limitation. Examples thereof include various alcohol-based solvents such as water, methanol, ethanol, propanol, 2-propanol, butanol, tert-butanol, tert-amyl alcohol, and 3,7-dimethyl-3-octanol; various aromatic hydrocarbon-based solvents such as benzene, toluene, and xylene; various aliphatic hydrocarbon-based solvents such as hexane, heptane, octane, decane, petroleum ether, kerosene, ligroin, and paraffin; various ketone-based solvents such as acetone, methyl ethyl ketone, and methyl isobutyl ketone; various ester-based solvents such as ethyl acetate, butyl acetate, methyl benzoate, dioctyl phthalate, and ethylene glycol diacetate; and various glycol ether-based solvents such as diethylether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, a polyethylene glycol-polypropylene glycol block copolymer, and a polyethylene glycol-polypropylene glycol random copolymer. These solvents can be used alone or in combination. Among these, water is most preferable. When irradiation with radiation is carried out in a state where a molding is immersed in an aqueous liquid, an aqueous liquid is suitably, in addition to pure water, saline, a phosphate-based buffer (preferably pH of 7.1 to 7.3), or a borate-based buffer (preferably pH of 7.1 to 7.3).

Irradiation with radiation in a state where a molding is sealed in a container has a merit capable of simultaneously performing sterilization of the molding.

γ rays are preferably used as radiations. In this case, too large γ dose may fail to obtain sufficient bonding between a molding and a coating layer, while too large γ dose may cause deterioration of physical properties of a molding. Therefore, the dose is preferably from 0.1 to 100 kGy, more preferably, from 15 to 50 kGy, and most preferably from 20 to 40 kGy. Thereby, at least a part inside a coating layer and at least a part of the space between a coating layer and a molding are crosslinked, thus enabling an improvement in resistance (for example, scrubbing resistance) of the coating layer. Meanwhile, crosslinking is also generated inside a molding by irradiating with radiation and thus the medical device may become too hard. In that case, it is possible to suppress excess crosslinking inside the molding by appropriately replacing a component A in the molding by a component M to thereby copolymerize the molding.

The medical device of the present invention is useful as low water content soft lenses for eye, for example, a lens for eye, such as a low water content soft contact lens, an intraocular lens, an artificial cornea, a corneal inlay, a corneal onlay, or a spectacle lens. Among these, a low water content soft contact lens is particularly preferable.

EXAMPLES

The present invention will be specifically described below byway of Examples, but the present invention is not limited thereto.
(Analytical Method and Evaluation Method)

As used herein, wet state means a state where a specimen is immersed in pure water or a borate buffer at room temperature (25° C.) for 24 hours or more. The measurement of mechanical properties in a wet state is carried out as soon as possible after pulling out the specimen from pure water or a borate buffer.

As used herein, dry state means a state where a specimen in a wet state is vacuum-dried at 40° C. for 16 hours. The degree of vacuum in the vacuum drying is set at 2 hPa or less. The measurement of mechanical properties in a dry state is carried out as soon as possible after the vacuum drying.

As used herein, a borate buffer is a "salt solution" disclosed in Example 1 of Kohyo (National Publication of Translated Version) No. 2004-517163. Specifically, it is an aqueous solution in which 8.48 g of sodium chloride, 9.26 g of boric acid, 1.0 g of sodium borate (sodium tetraborate decahydrate), and 0.10 g of ethylenediaminetetraacetic acid are dissolved in pure water to make 1,000 mL.

(1) Molecular Weight

Unless otherwise specified, polystyrene-equivalent mass average molecular weight and number average molecular weight were measured by a GPC method under the following conditions.
Pump: TOSOH DP-8020
Detector: TOSOH RI-8010
Column oven: Shimadzu CTO-6A
Auto-sampler: TOSOH AS-8010
Column: TOSOH TSKgel GMHHR-M (7.8 mm in inner diameter×30 cm,
5 μm in particle diameter)×two columns
Column temperature: 35° C.
Mobile phase: chloroform
Flow rate: 1.0 ml/minute
Sample concentration: 0.4% by mass
Injection amount: 100 μL
Standard sample: polystyrene (having a molecular weight of 1,010 to 1,090,000)
(2) Zero-Stress Time Zero-stress time was measured using a sample in a state of being wetted with a borate buffer. Strip-shaped samples of 5 mm in width and about 1.5 cm in length were cut out from near the center of a lens as a molding molded into a lens shape, and then measurement was carried out using a rheometer CR-500DX manufactured by Sun Scientific Co., Ltd. A chuck width was set at 5 mm and each sample was mounted, and then the operation of pulling at a speed of 100 mm/minute by 5 mm and returning to an initial length (5 mm) at the same speed was repeated three times. Length of time from a point of time at which stress during second returning to the initial length becomes zero to a point of time at which stress begins to be applied (stress increases from zero) after initiation of third pulling was determined, and the obtained length of time was regarded as a zero-stress time.
(3) Water Content A contact lens-shaped specimen was used. After immersing the specimen in a borate buffer and being left to stand in a constant-temperature bath at 40° C. for 24 hours or more, water on a surface was wiped off by a wiping cloth ("Kimwipe®", manufactured by NIPPON PAPER CRECIA Co., LTD.) and the mass (Ww) was measured. Then, the specimen was dried by a vacuum drying oven at 40° C. for 16 hours and the mass (Wd) was measured. Then, water content was determined by the following equation. In the case that the obtained value is less than 1%, it was judged to be unmesaurable and thus it was written as "less than 1%".

$$\text{Water content (\%)} = 100 \times (Ww - Wd)/Ww$$

(4) Wettability

A contact lens-shaped specimen was immersed in a borate buffer in a beaker at room temperature for 24 hours or more. The beaker containing the specimen and the borate buffer was exposed to ultrasonic using an ultrasonic cleaner (for 1 minute). The specimen was pulled up from the borate buffer and the specimen was held in air so that a surface becomes vertical. A state of the surface of the specimen was visually observed, and then judged by the following criteria. The diameter is a diameter of a circle formed by an edge portion of a contact lens.
A: A liquid film on a surface is held for 20 seconds or more.
B: A liquid film on a surface is broken within 10 to 20 seconds.
C: A liquid film on a surface is broken within 5 to 10 seconds.
D: A liquid film on a surface is broken within 1 to 5 seconds.

E: A liquid film on a surface is broken instantly (within 1 second).

(5) Measurement of Dynamic Contact Angle

Using samples in a state of being wetted with a borate buffer, the measurement was carried out, dynamic contact angle was measured by a dynamic wettability tester WET-6000 manufactured by RHESCA Corporation. Using, as dynamic contact angle samples, film-shaped specimens each measuring 5 mm×10 mm×about 0.1 mm cut out from samples molded into a film, or strip-shaped specimens of 5 mm in width cut out from contact lens-shaped samples, advancing dynamic contact angle relative to a borate buffer was measured. An immersion rate was set at 0.1 mm/sec, and an immerse depth was set at 7 mm.

(6) Tensile Elastic Modulus, Elongation

Using samples in a state of being wetted with a borate buffer, the measurement was carried out. Using a prescribed blanking die, specimens each measuring 5 mm in width (minimum portion), 14 mm in length and 0.2 mm in thickness were cut out from contact lens-shaped samples. Using the specimens, a tensile test was carried out by TENSILON, Model RTM-100, manufactured by ORIENTEC Co., Ltd. to thereby determine an elastic modulus (tensile elastic modulus) and an elongation (tensile elongation at break). A testing speed was 100 mm/minute, and a distance between grips (initial) was 5 mm.

(7) Lubricity

Lubricity was subjected to sensory evaluation after rubbing samples (contact lens shape) in a state of being wetted with a borate buffer five times with a finger of a person.
A: Excellent lubricity
B: About intermediate lubricity between A and C
C: Moderate lubricity
D: Little lubricity (about intermediate lubricity between C and E)
E: No lubricity (8) Scrubbing Resistance Samples (with contact lens shape) in a state of being wetted with a borate buffer were placed in the recess formed in the center of the flat of the hand and a cleaning solution ("ReNU®", Bausch & Lomb Incorporated) was added. After scrubbing front and back sides (each 10 times) by ball of the forefinger of another hand, samples were grasped by the thumb and forefinger and then both sides were further scrubbed 20 times while sprinkling the cleaning solution on the samples. The samples thus scrubbed were immersed in a borate buffer. Thereafter, (7) lubricity was evaluated.

(9) Surface Friction Coefficient

Figure 2:
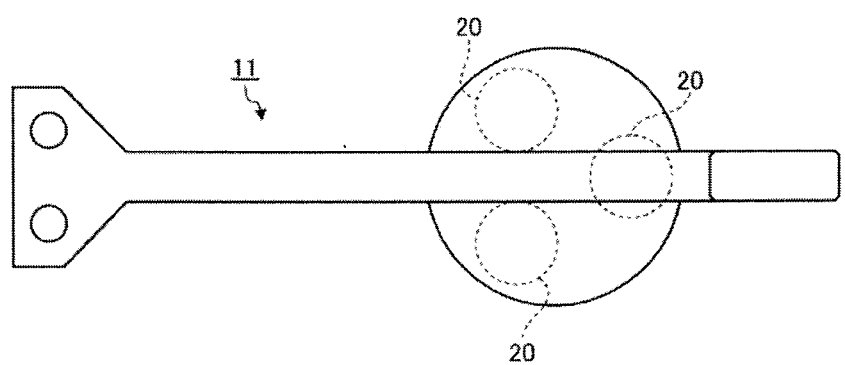
FIG. 2 is a schematic view showing the constitution of the main part of a measurement jig and a friction block for measuring a coefficient of surface friction of a sample of a medical device according to Example of the present invention, as seen from a direction A shown in FIG. 1.
Figure 3:
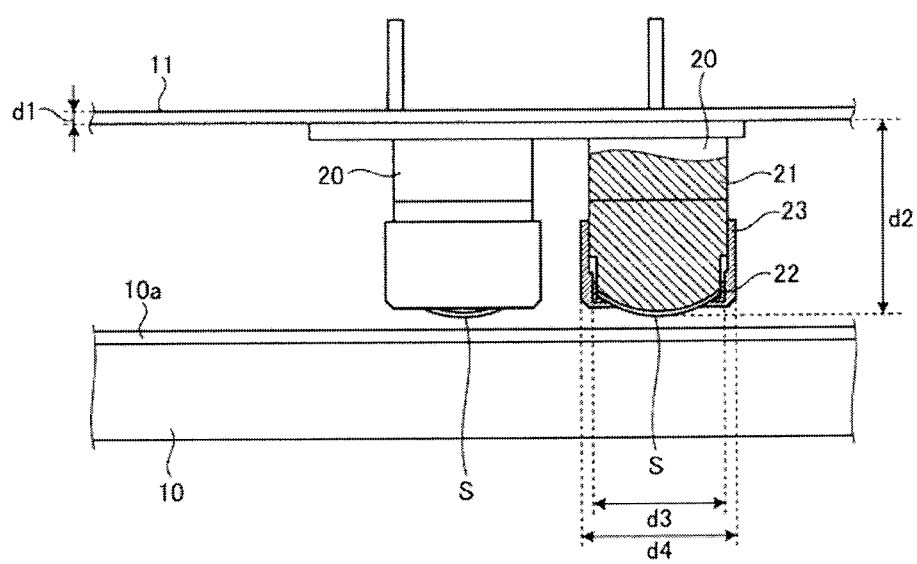
FIG. 3 is a partial cross-sectional view showing the constitution of the main part of a measurement jig and a friction block for measuring a coefficient of surface friction of a sample of a medical device according to Example of the present invention.

Using contact lens-shaped samples or film-shaped samples cut into a circle shape having a diameter of 14 mm, the measurement was carried out. Friction feeling tester KES-SE (Kato Tech Co., Ltd.) was used as a measurement apparatus. FIG. 1 is a schematic view showing an apparatus for measuring a surface friction coefficient. FIG. 2 is a schematic view showing the constitution of the main part of a measurement jig 11 and a friction block 20, as seen from a direction A shown in FIG. 1. FIG. 3 is a partial cross-sectional view showing the constitution of the main part of a measurement jig 11 and a friction block 20. First, a plate made of Teflon® (measuring 65 mm×100 mm×1.0 mm, omitted in FIG. 3) was horizontally disposed on a sample stand 10 of an apparatus 1, and then a quartz glass plate 10a having a smooth surface (measuring 55 mm×90 mm×1.0 mm) was horizontally disposed and fixed thereon. Plates having sufficiently high flatness were used as the plate made of Teflon® and the quartz glass plate. The quartz glass plate 10a is adjusted to a clean and dry wet by wiping off the surface with "Kimwipe" every measurement. In the measurement, three samples S were attached to a friction block 20 of a measurement jig 11 (weight of 62 g=W) shown in FIG. 2 and FIG. 3. At this time, the sample S were placed on tip of a mount holder 21 of the friction block 20, and then pressed by a packing 22 and fixed by a nut 23. In a state where the sample S is fixed while protruding from the end portion of the friction block 20, a borate buffer (each 0.1 mL) was dropped on each center portion of three samples under the following condition A, while a saline (each 0.1 mL) was dropped under the following condition B. Thereafter, the measurement jig 11 was quickly attached to the apparatus 1 and then stress (F) in a horizontal direction when the sample stand 10 is moved to a horizontal direction (arrow Y) at a rate of 1.0 mm/second in a state where all three samples S are contacted with the quartz glass plate 10a is detected by a friction detection unit 12 and measured by a dynamometer 13. The surface friction coefficient (MIU) was determined by the following equation.

$$MIU=F/W$$

A move distance was set at 30 mm and the measurement of MIU was carried out every 0.1 second.

The surface friction coefficient was an average value (value obtained by dividing the total of MIU in each time within a section by the number of data of MIU) of MIU in the section (at least 5 mm) where MIU at a move distance of 5 to 25 mm became stable.

At this time, a surface friction coefficient under the conditions A was MIUa, while a surface friction coefficient under the conditions B was MIUb.

Condition A: The measurement was carried out using samples in a state of being wetted with a borate buffer.

Condition B: The measurement was carried out using samples in a state of being wetted with a saline.

In FIG. 3, a thickness of a supporting plate which supports the friction block 20 of the measurement jig 11 is set at d1. In the friction block 20, when a protrusion length from the measurement jig 11 is d2, a diameter of the portion contacted with a lens of a mount holder 21 is d3, and a diameter of a periphery of a nut 23 is d4, d1=1.5 (mm), d2=22.4 (mm), d3=14 (mm), and d4=18 (mm).

(10) Surface Friction Coefficient Ratio

Surface friction coefficient (MIUo) of "ACUVUE® OASYS" (Johnson & Johnson Company) was measured by the method mentioned in (10) was measured under condition A. Surface friction coefficient ratios Qa and Qb were determined by the following equations.

$$Qa=MIUa/MIUo$$

$$Qb=MIUb/MIUo$$

Preparation of Molding

Reference Example 1

Polydimethylsiloxane having a methacryloyl group at one end (FM0705, CHISSO CORPORATION, mass average molecular weight of 930, number average molecular weight of 769) (5 parts by mass), as a component M, represented by the following formula (M2):

[Chemical Formula 7]

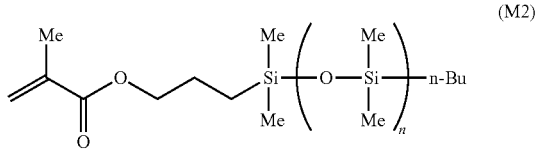

(M2)

polydimethylsiloxane having a methacryloyl group at both ends (FM7726, CHISSO CORPORATION, mass average molecular weight of 29 kD, number average molecular weight of 26 kD) (45 parts by mass), as a component A, represented by the following formula (A2):

[Chemical Formula 8]

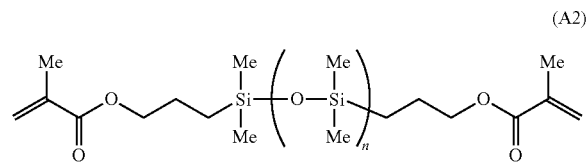

(A2)

trifluoroethyl acrylate (Viscoat 3F, Osaka Organic Chemical Industry Ltd.) (45 parts by mass) as a component B, methyl methacrylate (MMA, 0.5 part by mass) as a component Ck, an ultraviolet absorber having a polymerizable group (RUVA-93, Otsuka Chemical Co., Ltd.) (1 part by mass) as a component C, a polymerization initiator "IRGACURE®" 819 (Ciba Specialty Chemicals Inc., 1 part by mass), and t-amyl alcohol (10 parts by mass) were mixed and then stirred.

The insoluble matter was removed by filtering through a membrane filter (0.45 μm) to obtain a monomer mixture. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. Thereafter, in a glove box under a nitrogen atmosphere, the monomer mixture was injected into a mold for contact lens made of a transparent resin (poly-4-methylpentene-1). Using a fluorescent lamp (Toshiba Corporation, FL-6D, quasi-daylight, 6 W, 4 lamps), the monomer mixture was polymerized by irradiation with light (8,000 lux, 20 minutes). After polymerization, the whole mold was immersed in an aqueous 60% by mass isopropyl alcohol solution and a contact lens-shaped molding was removed from the mold. The obtained molding was immersed in a large excess amount of an aqueous 80% by mass isopropyl alcohol solution at 60° C. for 2 hours. Furthermore, the obtained molding was immersed in a large excess amount of an aqueous 50% by mass isopropyl alcohol solution at room temperature for 30 minutes, followed by immersion in a large excess amount of an aqueous 25% by mass isopropyl alcohol solution at room temperature for 30 minutes and further immersion in a large excess amount of pure water at room temperature for 30 minutes. Finally, the molding immersed in clean pure water was put in a closed vial bottle, and then autoclave sterilization was carried out at 121° C. for 30 minutes. The obtained molding included an edge portion having a diameter of about 14 mm and a center portion having a thickness of about 0.07 mm. The obtained molding had a water content of less than 1%. Using two glass plates and a gasket as a mold, a film-shaped sample measuring 60 mm×60 mm×0.25 mm was obtained by performing the same operation.

Reference Examples 2 to 12

In the very same manner as in Reference Example 1, except that the use amounts of the components M, A, and B were changed to amounts shown in Table 1, moldings were obtained. All moldings thus obtained had a water content of less than 1%.

TABLE 1

| | Component M | | Component A | | Component B | | Component C | | Component Ck RUVA-93 (Parts by mass) | Component Ck Acid treatment UniBlue A (Parts by mass) |
|---|---|---|---|---|---|---|---|---|---|---|
| | Name | Parts by mass | Name | Parts by mass | Name | Parts by mass | Name | Parts by mass | | |
| Reference Example 1 | FM0705 | 5 | FM7726 | 45 | Viscoat 3F | 48.5 | MMA | 0.5 | 1 | — |
| Reference Example 2 | FM0705 | 10 | FM7726 | 40 | Viscoat 3F | 48.5 | MMA | 0.5 | 1 | — |
| Reference Example 3 | FM0705 | 15 | FM7726 | 35 | Viscoat 3F | 48.5 | MMA | 0.5 | 1 | — |
| Reference Example 4 | FM0711 | 5 | FM7726 | 45 | Viscoat 3F | 48.5 | MMA | 0.5 | 1 | — |
| Reference Example 5 | FM0711 | 10 | FM7726 | 40 | Viscoat 3F | 48.5 | MMA | 0.5 | 1 | — |
| Reference Example 6 | FM0711 | 15 | FM7726 | 35 | Viscoat 3F | 48.5 | MMA | 0.5 | 1 | — |
| Reference Example 7 | FM0721 | 5 | FM7726 | 45 | Viscoat 3F | 48.5 | MMA | 0.5 | 1 | — |
| Reference Example 8 | FM0721 | 10 | FM7726 | 40 | Viscoat 3F | 48.5 | MMA | 0.5 | 1 | — |
| Reference Example 9 | FM0721 | 15 | FM7726 | 35 | Viscoat 3F | 48.5 | MMA | 0.5 | 1 | — |
| Reference Example 10 | FM0725 | 5 | FM7726 | 45 | Viscoat 3F | 48.5 | MMA | 0.5 | 1 | — |
| Reference Example 10 | FM0725 | 5 | FM7726 | 45 | Viscoat 3F | 48.5 | MMA | 0.5 | 1 | — |

TABLE 1-continued

| | | | | | | | | | | |
|---|---|---|---|---|---|---|---|---|---|---|
| Reference Example 11 | FM0725 | 10 | FM7726 | 40 | Viscoat 3F | 48.5 | MMA | 0.5 | 1 | — |
| Reference Example 12 | FM0725 | 15 | FM7726 | 35 | Viscoat 3F | 48.5 | MMA | 0.5 | 1 | — |
| Reference Example 15 | FM0721 | 10 | FM7726 | 40 | Viscoat 3F | 45 | 2-EHA/ DMAEA | 3/1 | 1 | 0.5 |
| Reference Example 13 | — | — | FM7726 | 50 | Viscoat 3F | 48.5 | MMA | 0.5 | 1 | — |
| Reference Example 14 | TRIS | 15 | FM7726 | 35 | Viscoat 3F | 48.5 | MMA | 0.5 | 1 | — |

| | Polymerization initiator | | Solvent | | Elongation (%) | Elastic modulus (MPa) | Zero-stress time (Sec) | Crosslinking density |
|---|---|---|---|---|---|---|---|---|
| | Name | Parts by mass | Name | Parts by mass | | | | |
| Reference Example 1 | IRGACURE 819 | 1 | TAA | 10 | 630 | 0.786 | — | 17.31 |
| Reference Example 2 | IRGACURE 819 | 1 | TAA | 10 | 770 | 0.572 | 0.85 | 15.38 |
| Reference Example 3 | IRGACURE 819 | 1 | TAA | 10 | 475 | 0.517 | 0.85 | 13.46 |
| Reference Example 4 | IRGACURE 819 | 1 | TAA | 10 | 736 | 0.669 | — | 17.31 |
| Reference Example 5 | IRGACURE 819 | 1 | TAA | 10 | 544 | 0.579 | — | 15.38 |
| Reference Example 6 | IRGACURE 819 | 1 | TAA | 10 | 475 | 0.517 | 0.84 | 13.46 |
| Reference Example 7 | IRGACURE 819 | 1 | TAA | 10 | 444 | 0.841 | 0.56 | 17.31 |
| Reference Example 8 | IRGACURE 819 | 1 | TAA | 10 | 705 | 0.814 | — | 15.38 |
| Reference Example 9 | IRGACURE 819 | 1 | TAA | 10 | 540 | 0.752 | 0.89 | 13.46 |
| Reference Example 10 | IRGACURE 819 | 1 | TAA | 10 | 513 | 0.807 | 0.70 | 17.31 |
| Reference Example 10 | IRGACURE 819 | 1 | TAA | 10 | 513 | 0.807 | 0.70 | 17.31 |
| Reference Example 11 | IRGACURE 819 | 1 | TAA | 10 | 518 | 0.689 | 0.81 | 15.38 |
| Reference Example 12 | IRGACURE 819 | 1 | TAA | 10 | 479 | 0.696 | 0.80 | 13.46 |
| Reference Example 15 | IRGACURE 819 | 1 | TAA | 10 | 511 | 0.579 | — | 15.31 |
| Reference Example 13 | IRGACURE 819 | 1 | TAA | 10 | 740 | 1.055 | 0.50 | 19.23 |
| Reference Example 14 | IRGACURE 819 | 1 | TAA | 10 | 730 | 0.490 | 1.01 | 13.46 |

FM0705: Compound of the formula (M2), Mw of 930, Mn of 769, CHISSO CORPORATION
FM0711: Compound of the formula (M2), Mw of 1,500, Mn of 1,300, CHISSO CORPORATION
FM0721: Compound of the formula (M2), Mw of 6,800, Mn of 6,500, CHISSO CORPORATION
FM0725: Compound of the formula (M2), Mw of 13,300, Mn of 12,800, CHISSO CORPORATION.

Reference Examples 13 to 14

In the very same manner as in Example 1, except that the component M is not contained and the use amount of the component A was changed to 50 parts by mass, a molding was obtained as Reference Example 13. All moldings thus obtained had a water content of less than 1%. In the very same manner as in Example 1, except that a branched silicone (TRIS) as a monofunctional monomer was mixed in the composition shown in Table 1 in place of the component M, a molding was obtained as Reference Example 14.

Reference Example 15

Polydimethylsiloxane having a methacryloyl group at one end (FM0721, CHISSO CORPORATION, mass average molecular weight of 68 kD, number average molecular weight of 65 kD) (10 parts by mass) represented by the formula (M2) shown below as a component M, polydimethylsiloxane having a methacryloyl group at both ends (FM7726, CHISSO CORPORATION, mass average molecular weight of 29 kD, number average molecular weight of 26 kD) (40 parts by mass) represented by the formula (A2) shown below as a component A, trifluoroethyl acrylate (Viscoat 3F, Osaka Organic Chemical Industry Ltd.) (45 parts by mass) as a component B, 2-ethylhexyl acrylate (2-EHA, 3 parts by mass) as a component C, N,N-dimethylaminoethyl acrylate (DMAEA, 1 part by mass) as a component C, an ultraviolet absorber having a polymerizable group (RUVA-93, Otsuka Chemical Co., Ltd.) (1 part by mass) as a component Ck, a colorant having a polymerizable group represented by the following estimated structural formula (C3H):

[Chemical Formula 9]

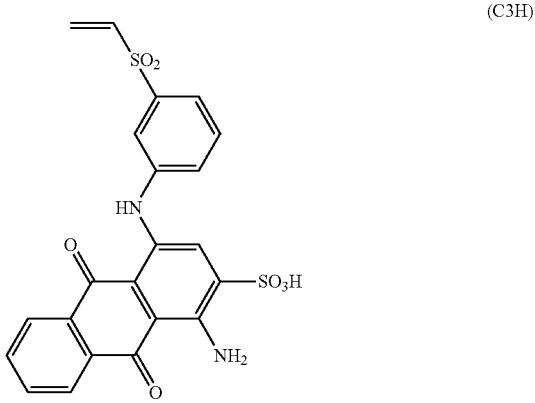

(C3H)

[those obtained by Uniblue A (Sigma-Aldrich Corporation) with hydrochloric acid] (0.5 part by mass), a polymerization initiator "IRGACURE®" 819 (Ciba Specialty Chemicals Inc., 1 part by mass), and t-amyl alcohol (10 parts by mass) as a solvent were mixed and then stirred. The insoluble matter was removed by filtering through a membrane filter (0.45 μm) to obtain a monomer mixture. This monomer mixture was charged in a test tube and degassing was carried out under reduced pressure of 20 Torr (27 hPa) while stirring using a touch mixer, and then the pressure was returned to atmospheric pressure using an argon gas. This operation was repeated three times. Thereafter, in a glove box under a nitrogen atmosphere, the monomer mixture was injected into a mold for contact lens made of a transparent resin (poly-4-methylpentene-1). Using a fluorescent lamp (Toshiba Corporation, FL-6D, quasi-daylight, 6 W, 4 lamps), the monomer mixture was polymerized by irradiation with light (8,000 lux, 20 minutes). After polymerization, the whole mold was immersed in an aqueous 60% by mass isopropyl alcohol solution and a contact lens-shaped molding was removed from the mold. The obtained molding was immersed in a large excess amount of an aqueous 80% by mass isopropyl alcohol solution at 60° C. for 2 hours. Furthermore, the obtained molding was immersed in a large excess amount of an aqueous 50% by mass isopropyl alcohol solution at room temperature for 30 minutes, followed by immersion in a large excess amount of an aqueous 25% by mass isopropyl alcohol solution at room temperature for 30 minutes and further immersion in a large excess amount of pure water at room temperature for 30 minutes. Finally, the molding immersed in clean pure water was put in a closed vial bottle, and then autoclave sterilization was carried out at 121° C. for 30 minutes.

The obtained molding included an edge portion having a diameter of about 14 mm and a center portion having a thickness of about 0.10 mm. The obtained molding had a water content of less than 1%, a tensile elastic modulus of 0.579 MPa, and an elongation at break of 511%, and it was transparent and free from white turbidity, and therefore suitable as a contact lens. Using two glass plates and a gasket as a mold, a film-shaped sample measuring 60 mm×60 mm×0.25 mm was obtained by performing the same operation.

Regarding the moldings obtained in Reference Examples 1 to 15, the evaluation results of elongation, elastic modulus, and zero-stress time are shown in Table 1.

(Synthesis of Polymer for Coating)

Synthesis Examples of copolymers used for coating in Examples are shown. In Synthesis Examples, molecular weight of each copolymer was measured under the following conditions.

The conditions for the measurement of GPC of the polymer for coating are as follows.
Apparatus: Prominence GPC system, manufactured by Shimadzu Corporation
Pump: LC-20AD
Auto-sampler: SIL-20AHT
Column oven: CTO-20A
Detector: RID-10A
Column: manufactured by TOSOH CORPORATION GMP-WXL (7.8 mm in inner diameter×30 cm, 13 μm in particle diameter)
Solvent: Water/methanol=1/1 (addition of 0.1N lithium nitrate)
Flow rate: 0.5 mL/minute
Measurement time: 30 minutes
Sample concentration: 0.1% by mass
Injection amount: 100 μL
Standard sample: Polyethylene oxide standard sample, manufactured by Agilent (0.1 kD to 1,258 kD)

Synthesis Example 1

CPDA: N,N-dimethylacrylamide/acrylic acid (Molar Ratio of 2/1)

In a 500 mL three-necked flask, N,N-dimethylacrylamide (59.50 g, 0.600 mol), acrylic acid (21.62 g, 0.300 mol), pure water (325.20 g), a polymerization initiator VA-061 (Wako Pure Chemical Industries, Ltd., 0.1408 g, 0.562 mmol), and 2-mercaptoethanol (43.8 μL, 0.63 mmol) were charged, and then equipped with a three-way stop-cock, a reflux condenser tube, a thermometer, and a mechanical stirrer. The concentration of the monomer was 20% by mass. After degassing inside the three-necked flask using a vacuum pump and repeating replacement by argon three times, stirring was carried out at 50° C. for 0.5 hour, followed by temperature rise to 70° C. and further stirring for 6.5 hours. After completion of the polymerization, the polymerization reaction solution was concentrated to 400 g by an evaporator and poured into a 2-propanol/n-hexane (=500 mL/500 mL). The mixed solution was left to stand, and then the supernatant was removed by decantation. The obtained solid component was washed three times with 2-propanol/n-hexane (=250 mL/250 mL). The solid component was dried overnight by a vacuum drying oven at 60° C. Liquid nitrogen was charged and the solid component was crushed by a spatula, and then dried by a vacuum drying oven at 60° C. for 3 hours. The thus obtained copolymer had a molecular weight of Mn: 55 kD, Mw: 192 kD (Mw/Mn=3.5).

(Preparation of Coating Solution)

Hereinafter, pure water means water purified by filtering through a reverse osmosis membrane.

<PEI Solution>
Polyethyleneimlne (P3143, Sigma-Aldrich Corporation, molecular weight of 750,000) was dissolved in pure water to obtain an aqueous 1% by mass solution.

<PAA Solution>
Polyacrylic acid (169-18591, Wako Pure Chemical Industries, Ltd., molecular weight 250,000) was dissolved in pure water to obtain an aqueous 1.2% by mass solution.

<CPDA Solution>

CPDA obtained in Synthesis Example 1 was dissolved in pure water to obtain an aqueous 1% by mass solution.

Examples 1 to 12, 14 and Comparative Examples 1 to 2

A layer made of an acidic polymer and a basic polymer (coating layer) was formed on the moldings obtained in Reference Examples 1 to 15. The molding obtained in Reference Example 1 was immersed in a PAA solution for 30 minutes and then respectively immersed in three pure water baths for 5 minutes. Next, the molding was immersed in a PEI solution A for 30 minutes and then respectively immersed in three pure water baths for 5 minutes. Next, the molding was immersed in a CPDA solution for 30 minutes and then respectively immersed in three pure water baths for 5 minutes, and then lubricity, wettability, and dynamic contact angle were evaluated (Example 1). In the same manner, a layer made of an acidic polymer and a basic polymer was formed on the moldings obtained in Reference Examples 2 to 14, and then lubricity, wettability, and dynamic contact angle were evaluated (Examples 2 to 12 and Comparative Examples 1 to 2). The evaluation results are shown in Table 2.

TABLE 2

| | Molding | Lubricity | Wettability | Dynamic contact angle (Advancing angle) | Scrubbing Resistance |
|---|---|---|---|---|---|
| Example 1 | Reference Example 1 | A | B | — | C |
| Example 2 | Reference Example 2 | A | B | — | C |
| Example 3 | Reference Example 3 | A | B | — | C |
| Example 4 | Reference Example 4 | A | B | — | C |
| Example 5 | Reference Example 5 | A | B | — | C |
| Example 6 | Reference Example 6 | A | B | — | C |
| Example 7 | Reference Example 7 | A | B | — | C |
| Example 8 | Reference Example 8 | A | B | — | C |
| Example 9 | Reference Example 9 | A | B | — | C |
| Example 10 | Reference Example 10 | A | B | — | C |
| Example 11 | Reference Example 11 | A | B | 60 | C |
| Example 12 | Reference Example 12 | A | B | 57 | C |
| Example 13 | Reference Example 12 | A | B | — | A |
| Example 14 | Reference Example 15 | A | B | — | C |
| Comparative Example 1 | Reference Example 13 | A | C | 76 | C |
| Comparative Example 2 | Reference Example 14 | A | B | — | C |

As compared with the molding obtained in Comparative Example 1, wettabilities of the moldings obtained in Example 1 to 12, and 14 were improved. When a comparison was made between dynamic contact angles of the moldings obtained in Examples 11 to 12 and Comparative Example 1, dynamic contact angles of the moldings of Examples 11 to 12 were reduced. These reasons are unclear but are considered that the moldings of Examples 1 to 12 and 14 exhibit stickiness on a surface at a stage before coating as compared with the molding of Comparative Example 1 before coating, and thus a coating polymer becomes easier to adhere due to stickiness.

Comparative Example 3

The molding obtained in Reference Example 12 was immersed in an aqueous 1% by mass PVP K90 solution (polyvinylpyrrolidone, Sigma-Aldrich Japan, molecular weight of 360,000) at room temperature for 30 minutes and then taken out from the solution, followed by touch with a finger of a person. As a result, the molding had extremely excellent lubricity. The lubricity was rated "A" according to criteria for evaluation of lubricity. Thereafter, the molding was lightly rinsed with pure water in a beaker, followed by touch with a finger of a person. As a result, the molding had no lubricity. The lubricity was rated "E" according to criteria for evaluation of lubricity.

Example 13

The molding obtained in Example 12 immersed in a borate buffer was put in a closed vial bottle, and then irradiated with γ ray. The γ dose was 35 kGy. The evaluation results of lubricity, wettability, dynamic contact angle, and scrubbing resistance are shown in Table 2.

Example 15

A coefficient of surface friction (MIUa) between the molding obtained in Example 14 and a smooth quartz glass plate in a state of being wetted with a borate buffer, and a coefficient of surface friction (MIUb) between the molding and a smooth quartz glass plate in a state of being wetted with a saline were measured. The measurement results are shown in Table 3.

TABLE 3

| Measurement sample | Example 15 | ACUVUE ® OASYS |
|---|---|---|
| Surface friction coefficient (Borate buffer) | 0.007 | 0.305 |
| Surface friction coefficient (Saline) | 0.023 | — |

The surface friction ratio was 0.6 or less when Qa=0.007/0.305=0.023, or 0.8 or less when Qb=0.023/0.305=0.075, and the molding exhibits satisfactory lubricity even when using any of the borate buffer and saline. It is considered that a difference in lubricity between during opening and use is small since Qb−Qa=0.052.

Comparative Example 4

Regarding the molding (before coating) obtained in Reference Example 15, the measurement was performed using a borate buffer in the same manner as in Example 15. As a result, the surface friction coefficient MIUa=2.638 and the surface friction ratio coefficient Qa=2.745/0.305=9.000, and thus they were inferior to those of Example 15.

Comparative Example 5

Regarding a commercially available silicone hydrogel soft contact lens product "O2 Optix®" (manufactured by CIBA Vision Corporation), the measurement was performed using a borate buffer in the same manner as in Example 15. As a result, the surface friction coefficient MIUa=2.638 and the surface friction ratio coefficient Qa=2.638/0.305=8.647, and thus they were inferior to those of Example 15.

The present invention is directed to a medical device and can be suitably used as a device which is used in contact with the patient, or which is used in contact with tissues collected from the patient, for example, blood or other body fluids, for example, a lens for eye or a skin material. The medical device is particularly useful as low water content soft lenses for eye, for example, a lens for eye, such as a low water content soft contact lens, an intraocular lens, an artificial cornea, a corneal inlay, a corneal onlay, or a spectacle lens.

REFERENCE SIGNS LIST

1 Apparatus
10 Sample stand
10a Quartz glass plate
11 Measurement jig (made of aluminum)
12 Friction detection unit
13 Dynamometer
20 Friction block
21 Mount holder (made of aluminum)
22 Packing (made of "Teflon®")
23 Nut (made of aluminum)
S Sample

The invention claimed is:

1. A medical device in which a layer made of an acidic polymer and a basic polymer is formed on at least a part of a low water content soft base material, the low water content soft base material containing, as a main component, a copolymer containing a component M, a component C, and a component A, wherein the content of the component M is from 5 to 200 parts by mass based on 100 parts by mass of the component A, wherein:
component M is a monofunctional monomer having one polymerizable functional group and one silicone moiety per molecule;
component C is a monomer selected from a group consisting of methyl (meth)acrylate, ethyl (meth)acrylate, n-propyl (meth)acrylate, n-butyl (meth)acrylate, tert-butyl(meth)acrylate, isobutyl (meth)acrylate, n-hexyl (meth)acrylate), n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, and n-stearyl(meth)acrylate;
component A is a polysiloxane compound having a plurality of polymerizable functional groups per molecule and a number average molecular weight of 6,000 or more; and
wherein the medical device has a water content of 2% by mass or less.

2. The medical device according to claim 1, wherein the base material has a crosslinking degree of 2.0 to 18.3, provided that the crosslinking degree is represented by the following formula (Q1):

$$\text{Crosslinking degree} = \frac{\sum_{n=1}^{\infty} \{Qn \times (n-1)\}}{\sum_{n=1}^{\infty} Wn} \quad (Q1)$$

where Qn represents a total millimolar amount of a monomer having n polymerizable groups per molecule, Wn represents a total mass (kg) of a monomer having n polymerizable groups per molecule and, when a molecular weight of the monomer has distribution, the millimolar amount is calculated using a number average molecular weight.

3. The medical device according to claim 1, wherein the silicone moiety is linear.

4. The medical device according to claim 1, wherein the monofunctional monomer component M is a component represented by the following formula (M1):

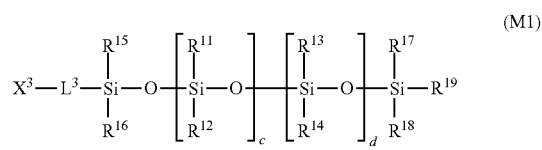

wherein $X^3$ represents a polymerizable functional group; $R^{11}$ to $R^{19}$ each independently represents a substituent selected from hydrogen, an alkyl group having 1 to 20 carbon atoms, a phenyl group, and a fluoroalkyl group having 1 to 20 carbon atoms; $L^3$ represents a divalent group; and c and d each independently represents an integer of 0 to 700, provided that c and d are not simultaneously 0.

5. The medical device according to claim 1, wherein the base material contains, as a main component:
a copolymer containing the component M, the component C, the component A, and a component B, wherein component B is a polymerizable monomer having a fluoroalkyl group.

6. The medical device according to claim 5, wherein the polymerizable functional group of the component A is a polymerizable functional group copolymerizable with the polymerizable functional group of the component M.

7. The medical device according to claim 5, wherein a mass ratio of the component M to the component A is 5 to 200 parts by mass of the component M/100 parts by mass of the component A.

8. The medical device according to claim 1, wherein the layer made of an acidic polymer and a basic polymer is formed of only one kind of an acidic polymer and one kind of a basic polymer.

9. The medical device according to claim 1, wherein the layer made of an acidic and a basic polymer is formed of two kinds of acidic polymers and one kind of a basic polymer.

10. The medical device according to claim 1, wherein at least one of the acidic polymer and the basic polymer, which compose the layer made of an acidic and a basic polymer, is a polymer having a group selected from a hydroxyl group and an amide group.

11. The medical device according to claim 1, which is a low water content soft lens for eye.

12. A method for producing a medical device, the medical device having a water content of 2% by mass or less, which comprises the following steps 1a to 3a in this order:
<Step 1a>
Step of polymerizing a mixture to obtain a molding, the mixture comprising:
component M: a monofunctional monomer having one polymerizable functional group and one silicone moiety per molecule;
component C: a monomer selected from a group consisting of methyl (meth)acrylate, ethyl (meth)acrylate, n-propyl (meth)acrylate, n-butyl (meth)acrylate, tert-butyl (meth)acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate and n-stearyl (meth)acrylate; and component A: a polysiloxane compound having a plurality of polymerizable functional groups per molecule and a number average molecular weight of 6,000 or more;

wherein the content of the component M is from 5 to 200 parts by mass based on 100 parts by mass of the component A;

<Step 2a>

Step of bringing the molding into contact with a basic polymer solution, and then washing the molding to remove the surplus basic polymer solution; and <Step 3a>

Step of bringing the molding into contact with an acidic polymer solution, and then washing the molding to remove the surplus acidic polymer solution.

13. A method for producing a medical device, the medical device having a water content of 2% by mass or less, which comprises the following steps 1b to 4b in this order:

<Step 1b>

Step of polymerizing a mixture to obtain a molding, the mixture comprising:

component M: a monofunctional monomer having one polymerizable functional group and one silicone moiety per molecule, component C: a monomer selected from a group consisting of methyl (meth)acrylate, ethyl (meth)acrylate, n-propyl (meth)acrylate, n-butyl (meth)acrylate, tert-butyl (meth)acrylate, isobutyl (meth)acrylate, n-hexyl (meth)acrylate, n-octyl (meth)acrylate 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl and n-stearyl (meth)acrylate; and component A: a polysiloxane compound having a plurality of polymerizable functional groups per molecule and a number average molecular weight of 6,000 or more;

wherein the content of the component M is from 5 to 200 parts by mass based on 100 parts by mass of the component A;

<Step 2b>

Step of bringing the molding into contact with an acidic polymer solution, and then washing the molding to remove the surplus acidic polymer solution;

<Step 3b>

Step of bringing the molding into contact with a basic polymer solution, and then washing the molding to remove the surplus basic polymer solution; and <Step 4b>

Step of bringing the molding into contact with an acidic polymer solution, and then washing the molding to remove the surplus acidic polymer solution.

14. The method for producing a medical device according to claim 12, wherein the mixture further contains a component B which is a polymerizable monomer having a fluoroalkyl group.

15. The method for producing a medical device according to claim 13, wherein the mixture further contains a component B which is polymerizable monomer having a fluoroalkyl group.

* * * * *